United States Patent
Staid et al.

(10) Patent No.: US 12,419,701 B2
(45) Date of Patent: *Sep. 23, 2025

(54) SURGICAL PROBES FOR TISSUE RESECTION WITH ROBOTIC ARMS

(71) Applicant: PROCEPT BioRobotics Corporation, Redwood City, CA (US)

(72) Inventors: Kevin Patrick Staid, Lowell, MA (US); Surag Mantri, East Palo Alto, CA (US); Nikolai Aljuri, Hillsborough, CA (US)

(73) Assignee: PROCEPT BioRobotics Corporation, San Jose, CA (US)

( * ) Notice: Subject to any disclaimer, the term of this patent is extended or adjusted under 35 U.S.C. 154(b) by 1037 days.

This patent is subject to a terminal disclaimer.

(21) Appl. No.: 17/304,571

(22) Filed: Jun. 23, 2021

(65) Prior Publication Data

US 2021/0378766 A1    Dec. 9, 2021

Related U.S. Application Data

(63) Continuation of application No. 16/939,972, filed on Jul. 27, 2020, now Pat. No. 11,071,601.
(Continued)

(51) Int. Cl.
*A61B 34/30* (2016.01)
*A61B 17/32* (2006.01)
*A61B 17/3203* (2006.01)

(52) U.S. Cl.
CPC ...... *A61B 34/30* (2016.02); *A61B 17/320016* (2013.01); *A61B 17/3203* (2013.01);
(Continued)

(58) Field of Classification Search
CPC ............ A61B 34/30; A61B 17/320016; A61B 17/3203; A61B 2034/301; A61B 2017/320064
See application file for complete search history.

(56) References Cited

U.S. PATENT DOCUMENTS

| 4,389,071 A | 6/1983 | Johnson, Jr. |
| 4,561,798 A | 12/1985 | Elcrin |

(Continued)

FOREIGN PATENT DOCUMENTS

| CN | 101394877 | 3/2009 |
| CN | 102905633 | 1/2013 |

(Continued)

OTHER PUBLICATIONS

Office Action (Non-Final) for U.S. Appl. No. 16/940,085, 10 pages (May 25, 2022).

(Continued)

*Primary Examiner* — Mohamed G Gabr
*Assistant Examiner* — Khoa Tan Le
(74) *Attorney, Agent, or Firm* — Knobbe, Martens, Olson & Bear, LLP

(57) ABSTRACT

An energy source is coupled to a probe mounted on a robotic arm, and a processor configured with instructions to release energy to resect tissue in coordination with movement of the robotic arm and probe. The tissue can be resected in accordance with a defined tissue resection volume that can be determined based on images of the patient. The probe can be moved to a plurality of positions with movement of a distal end of the robotic arm and tissue resected in accordance with the treatment plan. The distal end of the robotic arm can be configured to move to a plurality of locations and orientations to provide an appropriate position and orientation of the probe tip and energy source. The processor can be configured with instructions to pivot the probe at a location to decrease tissue movement near the pivot such as an internal location of the patient.

21 Claims, 22 Drawing Sheets

Related U.S. Application Data

(60) Provisional application No. 62/933,721, filed on Nov. 11, 2019.

(52) U.S. Cl.
CPC ............ *A61B 2017/320064* (2013.01); *A61B 2034/301* (2016.02)

(56) References Cited

U.S. PATENT DOCUMENTS

| | | | |
|---|---|---|---|
| 4,932,956 A | 6/1990 | Reddy | |
| 5,876,325 A | 3/1999 | Mizuno | |
| 6,039,695 A | 3/2000 | Sakamoto | |
| 6,331,181 B1 | 12/2001 | Tierney | |
| 6,338,714 B1 | 1/2002 | Krause | |
| 6,375,635 B1 | 4/2002 | Moutafis | |
| 7,021,173 B2 | 4/2006 | Stoianovici | |
| 7,806,957 B1 | 10/2010 | Burke | |
| 7,882,841 B2 | 2/2011 | Aljuri | |
| 8,062,246 B2 | 11/2011 | Moutafis | |
| 8,152,816 B2 | 4/2012 | Tuma | |
| 8,229,188 B2 | 7/2012 | Rusko | |
| 8,398,541 B2 | 3/2013 | Dimaio | |
| 8,660,635 B2 | 2/2014 | Simon | |
| 8,814,921 B2 | 8/2014 | Aljuri | |
| 8,827,948 B2 | 9/2014 | Romo | |
| 8,961,533 B2 | 2/2015 | Stahler | |
| 9,072,452 B2 | 7/2015 | Vayser | |
| 9,144,461 B2 | 9/2015 | Kruecker | |
| 9,277,969 B2 | 3/2016 | Brannan | |
| 9,314,306 B2 | 4/2016 | Yu | |
| 9,364,251 B2 | 6/2016 | Aljuri | |
| 9,610,131 B2 | 4/2017 | Stoianovici | |
| 9,737,371 B2 | 8/2017 | Romo | |
| 9,867,635 B2 | 1/2018 | Alvarez | |
| 9,877,788 B2 | 1/2018 | Stoianovici | |
| 10,130,427 B2 | 11/2018 | Tanner | |
| 10,226,298 B2 | 3/2019 | Ourselin | |
| 10,231,867 B2 | 3/2019 | Alvarez | |
| 10,307,214 B2 | 6/2019 | Lathrop | |
| 10,423,757 B2 | 9/2019 | Kruecker | |
| 10,441,371 B2 | 10/2019 | Hendrick | |
| 10,448,956 B2 | 10/2019 | Gordon | |
| 10,555,780 B2 | 2/2020 | Tanner | |
| 10,555,785 B2 | 2/2020 | Yeung | |
| 10,646,295 B2 | 5/2020 | Stoianovici | |
| 10,779,897 B2 | 9/2020 | Rockrohr | |
| 11,071,601 B2* | 7/2021 | Staid | A61B 17/3203 |
| 11,096,753 B1 | 8/2021 | Mantri | |
| 11,278,451 B2 | 3/2022 | Andrews | |
| 11,357,586 B2 | 6/2022 | Huang | |
| 11,590,319 B2 | 2/2023 | Debuys | |
| 11,771,512 B2 | 10/2023 | Mantri | |
| 12,178,537 B2 | 12/2024 | Mantri | |
| 2002/0121577 A1 | 9/2002 | Metelski | |
| 2004/0024311 A1 | 2/2004 | Quaid | |
| 2004/0034282 A1 | 2/2004 | Quaid | |
| 2004/0230211 A1 | 11/2004 | Moutafis | |
| 2006/0118495 A1 | 6/2006 | Kondratalv | |
| 2006/0142657 A1 | 6/2006 | Quaid | |
| 2006/0205996 A1 | 9/2006 | Presthus | |
| 2008/0009747 A1 | 1/2008 | Saadat | |
| 2008/0027420 A1 | 1/2008 | Wang | |
| 2009/0227998 A1 | 9/2009 | Aljuri | |
| 2009/0306692 A1 | 12/2009 | Barrington | |
| 2009/0326489 A1 | 12/2009 | Kensy | |
| 2010/0010524 A1 | 1/2010 | Barrington | |
| 2010/0036245 A1 | 2/2010 | Yu | |
| 2011/0184391 A1 | 7/2011 | Aljuri | |
| 2011/0282356 A1 | 11/2011 | Solomon | |
| 2012/0035462 A1 | 2/2012 | Maurer, Jr. | |
| 2012/0071894 A1 | 3/2012 | Tanner | |
| 2012/0095498 A1 | 4/2012 | Stefanchik | |
| 2013/0218186 A1 | 8/2013 | Dubois | |
| 2013/0239392 A1 | 9/2013 | Solomon | |
| 2014/0039314 A1 | 2/2014 | Stoianovici | |
| 2014/0094968 A1 | 4/2014 | Taylor | |
| 2014/0142438 A1 | 5/2014 | Ludwin | |
| 2014/0194896 A1 | 7/2014 | Frimer | |
| 2014/0309649 A1 | 10/2014 | Alvarez | |
| 2015/0025539 A1 | 1/2015 | Alvarez | |
| 2015/0080907 A1 | 3/2015 | Herrell | |
| 2015/0088107 A1 | 3/2015 | Aljuri | |
| 2015/0173726 A1 | 6/2015 | Lohmeier | |
| 2015/0351857 A1 | 12/2015 | Vander Poorten et al. | |
| 2015/0366546 A1 | 12/2015 | Kamen | |
| 2016/0067450 A1 | 3/2016 | Kowshik | |
| 2016/0100898 A1 | 4/2016 | Jinno | |
| 2016/0143778 A1 | 5/2016 | Aljuri | |
| 2016/0262827 A1 | 9/2016 | Ross | |
| 2016/0302653 A1 | 10/2016 | Inoue | |
| 2017/0014269 A1 | 1/2017 | Draheim | |
| 2017/0020253 A1 | 1/2017 | Drozdowicz | |
| 2017/0105785 A1 | 4/2017 | Shelton, IV | |
| 2017/0112577 A1* | 4/2017 | Bonutti | A61B 90/37 |
| 2017/0189127 A1 | 7/2017 | Weir | |
| 2017/0202537 A1 | 7/2017 | Ippolito | |
| 2017/0245878 A1 | 8/2017 | Aljuri | |
| 2017/0245949 A1 | 8/2017 | Randle | |
| 2017/0273797 A1 | 9/2017 | Gordon | |
| 2018/0014891 A1 | 1/2018 | Krebs | |
| 2018/0021960 A1 | 1/2018 | Grant | |
| 2018/0028261 A1 | 2/2018 | Chen | |
| 2018/0263647 A1 | 9/2018 | Aljuri | |
| 2018/0263685 A1 | 9/2018 | Onik | |
| 2018/0318011 A1 | 11/2018 | Leibinger | |
| 2018/0353253 A1* | 12/2018 | Bowling | A61B 34/30 |
| 2019/0015166 A1 | 1/2019 | Mahoney | |
| 2019/0021753 A1 | 1/2019 | Jinno | |
| 2019/0076674 A1 | 3/2019 | Ergün | |
| 2019/0105023 A1 | 4/2019 | Aljuri | |
| 2019/0105117 A1 | 4/2019 | Brisson | |
| 2019/0142396 A1 | 5/2019 | Stoianovici | |
| 2019/0151148 A1 | 5/2019 | Alvarez | |
| 2019/0201214 A1 | 7/2019 | Miller | |
| 2019/0202066 A1 | 7/2019 | Maret | |
| 2019/0223967 A1 | 7/2019 | Abbott | |
| 2019/0231450 A1 | 8/2019 | Waterbury | |
| 2019/0262057 A1 | 8/2019 | Grant | |
| 2019/0321119 A1 | 10/2019 | Yeung | |
| 2019/0336238 A1 | 11/2019 | Yu | |
| 2020/0008874 A1 | 1/2020 | Barbagli | |
| 2020/0020249 A1 | 1/2020 | Jarc | |
| 2020/0138454 A1 | 5/2020 | Patel | |
| 2020/0197108 A1 | 6/2020 | Usui | |
| 2020/0261297 A1 | 8/2020 | Strydom | |
| 2020/0360097 A1 | 11/2020 | Dimaio | |
| 2020/0360100 A1 | 11/2020 | Mantri | |
| 2020/0405403 A1 | 12/2020 | Shelton, IV | |
| 2021/0030496 A1 | 2/2021 | Devengenzo | |
| 2021/0137612 A1 | 5/2021 | Staid | |
| 2021/0401521 A1 | 12/2021 | Mantri | |
| 2021/0401522 A1 | 12/2021 | Mantri | |
| 2022/0273166 A1 | 9/2022 | Nord | |

FOREIGN PATENT DOCUMENTS

| | | |
|---|---|---|
| CN | 105764436 A | 7/2016 |
| CN | 105848552 | 8/2016 |
| CN | 109662779 | 4/2019 |
| CN | 111449694 | 7/2020 |
| EP | 1486900 | 12/2004 |
| JP | H07136173 | 5/1995 |
| JP | H7136173 | 5/1995 |
| JP | 2010142575 | 7/2010 |
| JP | 2015123201 | 7/2015 |
| JP | 2016502411 | 1/2016 |
| JP | 2017510826 | 4/2017 |
| JP | 2018198750 | 12/2018 |
| JP | 2019055287 | 4/2019 |
| NL | 1019547 | 5/2003 |
| WO | 2004004914 | 1/2004 |
| WO | 2008083407 | 7/2008 |
| WO | 2009111736 | 9/2009 |

(56) References Cited

FOREIGN PATENT DOCUMENTS

| | | |
|---|---|---|
| WO | 2011097505 | 8/2011 |
| WO | 2013053614 | 4/2013 |
| WO | 2013130895 | 9/2013 |
| WO | 2014092197 | 6/2014 |
| WO | 2014127242 | 8/2014 |
| WO | 2014165703 | 10/2014 |
| WO | 2015035249 | 3/2015 |
| WO | 2015137038 | 9/2015 |
| WO | WO 2015/158756 A1 | 10/2015 |
| WO | 2015200538 | 12/2015 |
| WO | 2016004071 | 1/2016 |
| WO | 2016037132 | 3/2016 |
| WO | 2016037137 | 3/2016 |
| WO | 2016054256 | 4/2016 |
| WO | 2016187290 | 11/2016 |
| WO | 2017161331 | 9/2017 |
| WO | 20170192603 | 9/2017 |
| WO | 2017187795 | 11/2017 |
| WO | 2018013848 | 1/2018 |
| WO | 2018216382 | 11/2018 |
| WO | 2019032986 | 2/2019 |
| WO | 2019137665 | 7/2019 |
| WO | 2019246580 | 12/2019 |
| WO | 2020180724 | 9/2020 |
| WO | 2020181278 | 9/2020 |
| WO | 2020181280 | 9/2020 |
| WO | 2020181281 | 9/2020 |
| WO | 2020181290 | 9/2020 |
| WO | 2021130229 | 7/2021 |

OTHER PUBLICATIONS

Notice of Allowance for U.S. Appl. No. 17/304,572, 8 pages (Feb. 27, 2023).
Office Action (Non-Final) for U.S. Appl. No. 16/940,100, 12 pages (Dec. 7, 2020).
Office Action (Non-Final) for U.S. Appl. No. 16/940,100, 13 pages (Dec. 20, 2021).
Office Action (Non-Final) for U.S. Appl. No. 16/940,100, 16 pages (Feb. 23, 2023).
Office Action (Non-Final) for U.S. Appl. No. 17/304,572, 8 pages (Nov. 29, 2022).
Office Action (Non-Final) for U.S. Appl. No. 16/940,085, 14 pages (Dec. 22, 2020).
Response to Non-Final Office Action for U.S. Appl. No. 16/940,100, 8 pages (Mar. 11, 2021).
Christoforou et al., Robotic Arm for Magnetic Resonance Imaging Guided Interventions, 2006, IEEE, p. 1-6 (Year: 2006).
Dwyer et al., A miniaturised robotic probe for real-time intraoperative fusion of ultrasound and endomicroscopy, 2015, IEEE, pg. ( Year: 2015).
International Search Report and Written Opinion for PCT/US2020/058884, 11 pages (Feb. 1, 2021).
Lim et al. "Robotic Transrectal Ultrasound-Guided Prostate Biopsy." IEEE Trans BME. Jan. 7, 2019. 11 pages. (Year: 2019).
Marmol etal., ArthroSLAM: Multi-Sensor Robust Visual Localization for Minimally Invasive Orthopedic Surgery, 2018, IEEE, p. 3882-3889 (Year: 2018).
Office Action (Final) for U.S. Appl. No. 16/940,085, 14 pages (Apr. 13, 2021).
Response to Final Office Action for U.S. Appl. No. 16/940,085, 8 pages (Jun. 3, 2021).
Response to Non-Final Office Action for U.S. Appl. No. 16/940,085, 8 pages (Mar. 2, 2021).
Rosa et al., Laparoscopic optical biopsies: In vivo robotized mosaicing with probe-based confocal endomicroscopy, 2011, IEEE, p. 1339-1345 (Year: 2011).
Stoianovici et al. "MRI-Safe Robot for Endorectal Prostate Biopsy." IEEE/ASME Trans Mechatronics, vol. 19, No. 4 Aug. 2014. pp. 1289-1299. (Year: 2014).
Office Action (Final) for U.S. Appl. No. 16/940,100, 15 pages (May 4, 2022).
Response to Non-Final Office Action for U.S. Appl. No. 16/940,100, 11 pages (Apr. 20, 2022).
Jakopec et al., Acrobot: a "hands-on" robot for total knee replacement surgery, 2002, IEEE, p. 116-120 (Year: 2002).
Non-Final Office Action for U.S. Appl. No. 16/940,085, 14 pages (Jun. 23, 2023).
Notice of Allowance for U.S. Appl. No. 17/304,572, 9 pages (Jun. 5, 2023).
Chirstoforou et al., Manipulator for magnetic resonance imaging guided interventions: design, prototype and feasibility, 2006, IEEE p. 3838-3843 (Year: 2006).
Xiao et al., Ultrasound Guided Robotic System for Transperineal Biopsy of the Prostate, 2006, IEEE, p. 1315-1320 (Year: 2006).
Office Action (Final) for U.S. Appl. No. 16/940,085, 11 pages (Sep. 29, 2022).
Caponero, M.A., et al., "Fabrication and calibration of three temperature probes for monitoring the effects of thermal cancer ablation," 2017, IEEE, pp. 1-5 (2017).
Elek et al., Robotic platforms for ultrasound diagnostics and treatment, 2017, IEEE, p. 1752-1757 (Year: 2017).
Priester et al., Robotic ultrasound systems in medicine, 2013, IEEE, p. 507-523 (Year: 2013).
Sen et al., A cooperatively controlled robot for ultrasound monitoring of radiation therapy, 2013, IEEE, p. 3071-3076 (Year: 2013).
Venkatesan; et al., Nanorobots in cancer treatment, 2010, IEEE, p. 258-264 (Year: 2010).

* cited by examiner

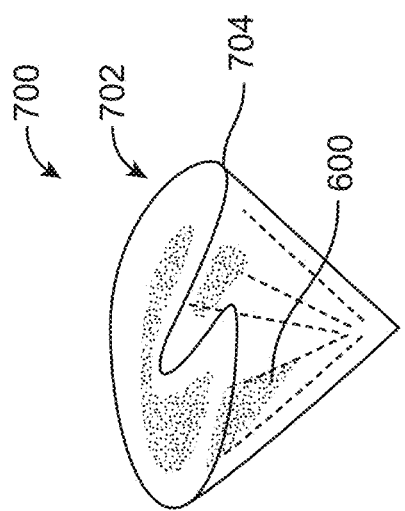
FIG. 7C
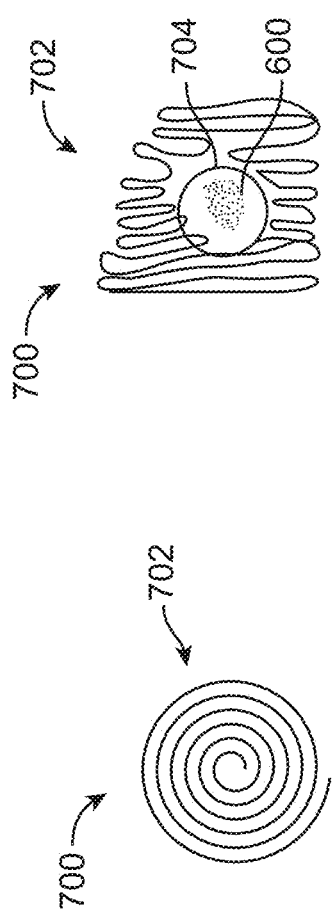
FIG. 7B
FIG. 7A
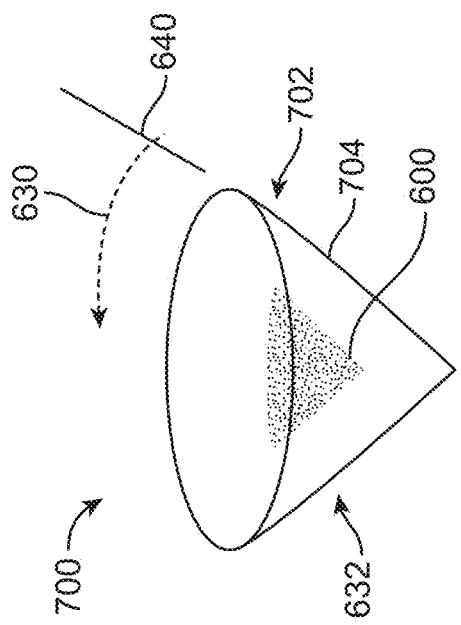
FIG. 7D

SURGICAL PROBES FOR TISSUE RESECTION WITH ROBOTIC ARMS

RELATED APPLICATIONS

This application is a continuation of U.S. patent application Ser. No. 16/939,972, filed Jul. 27, 2020, now U.S. Pat. No. 11,071,601, issued Jul. 27, 2021, which application claims the benefit under 35 U.S.C. § 119 (e) of U.S. Provisional Patent Application No. 62/933,721, filed Nov. 11, 2019, entitled "Surgical Probes for Tissue Resection with Robotic Arms", the entire disclosures of which are incorporated herein by reference.

BACKGROUND

Prior methods and apparatus for resecting tissue can be less than ideal in at least some respect. Although robotic arms have been used for surgery, prior surgical instruments coupled to robotic arms can be less than ideal in at least some instances. For example, at least some of the prior surgical instruments coupled to robotic arms may non-selectively resect tissue in at least some instances. Also the prior surgical instruments may be somewhat more complex than would be ideal when placed on a robotic arm.

Although prior robotic arms have been used to perform surgery with an operator moving the surgical instrument on the robotic arm with a controller, at least some of the prior approaches have less than ideally used imaging and image guidance to guide the probe to a target site to resect tissue.

In light of the above improved systems, methods and apparatus for improved tissue resection would be beneficial.

SUMMARY

The presently disclosed systems, methods and apparatus can be used to provide improved surgical procedures. In some embodiments, an energy source is coupled to a probe mounted on a robotic arm, and a processor configured with instructions to release energy so as to selectively resect tissue in coordination with movement of the robotic arm and probe. The tissue can be resected in accordance with a defined tissue resection volume that can be determined based on images of the patient. The probe can be moved to a plurality of positions with movement of a distal end of the robotic arm and tissue resected in accordance with the treatment plan. The distal end of the robotic arm can be configured to move to a plurality of locations and orientations to provide an appropriate position and orientation of the probe tip and energy source. In some embodiments, the processor is configured with instructions to pivot the probe at a location to decrease tissue movement near the pivot, and the pivot location may comprise an internal location of the patient. In some embodiments, the energy source of the treatment probe is configured to rotate while the distal end of the robotic arm remains at a fixed location and orientation. Alternatively, the robotic arm can be configured to rotate so as to rotate the energy source about an elongate axis of the treatment probe.

In some embodiments, the probe coupled to the distal end of the robotic arm comprises an irrigation lumen, and aspiration lumen, an endoscope and an energy source. The irrigation lumen and aspiration lumen can be used to provide a beneficial environment at the location where tissue is removed. In some embodiments, an enclosure such as a cup comprises an aperture to receive the treatment probe, and the enclosure comprises a barrier material to contain the fluid provided by the aspiration lumen.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 7A shows a tissue resection profile, in accordance with some embodiments;

FIG. 7B shows a tissue resection profile to remove tissue away from a tumor, in accordance with some embodiments;

FIG. 7C shows a 3D tissue resection profile around a tumor to remove tissue away from the tumor, in accordance with some embodiments;

FIG. 7D shows a conical tissue resection profile to remove tissue away from a tumor, in accordance with some embodiments;

FIGS. 9 to 12B show a method of tissue resection with a water jet, in accordance with some embodiments;

DETAILED DESCRIPTION

Figure 1:
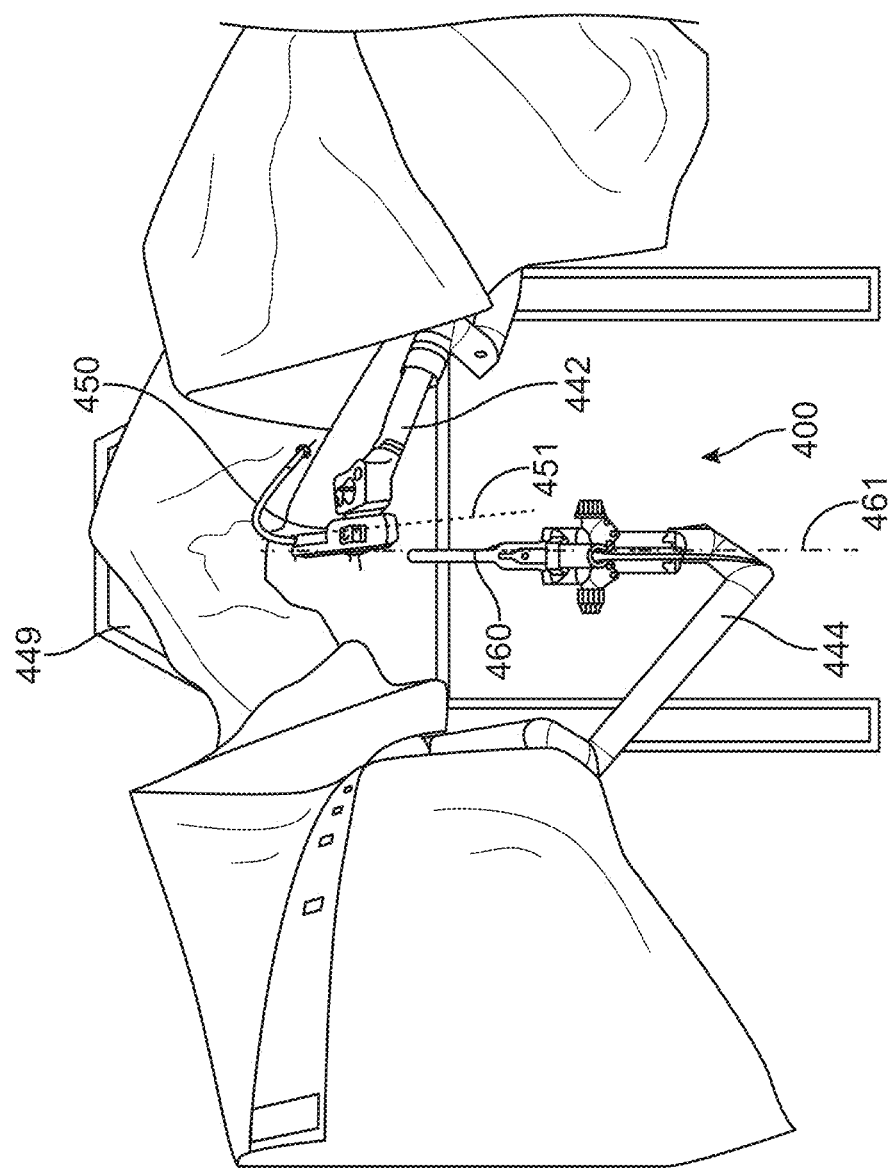
FIG. 1 shows a front view of a system for performing tissue resection in a patient, in accordance with some embodiments.

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

Embodiments of the present disclosure provide improved methods and apparatus for performing tissue resection, such as prostate tissue resection. The methods and apparatus disclosed herein are well suited for many types of surgical procedures, and can be incorporated into many prior systems and methods. While some embodiments of the present disclosure are directed to transurethral treatment of the prostate, some aspects of the present disclosure may also be used to treat and modify other tissues and associated organs. These other tissues and associate organs include but are not limited to the brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. The devices disclosed herein may be inserted through an existing body lumen, or inserted through an opening created in body tissue.

The presently disclosed methods and apparatus are well suited for treating many types of tissue with an energy source. The tissue may comprise soft tissue, such as glandular tissue or capsular tissue, or hard tissue such as bone or blockages, such as kidney stones, for example. The energy source may comprise one or more of a laser beam, a water jet, an electrode, ultrasound, high intensity focused ultrasound, mechanical vibrations, radiofrequency (RF) energy an ultrasound transducer, microwave energy, cavitating energy such as a cavitating water jet or ultrasonic cavitations, radiation such as ionizing radiation from a radioisotope, or ion energy from ionization electrodes or plasma energy from plasma electrodes. The presently disclosed methods and apparatus are well suited for performing lithotripsy to break up kidney stones, for example. The presently disclosed methods and apparatus are well suited for treatment with radiation, such as a radio isotope on the treatment probe. The radiation treatment can be provided on the probe and removed with the probe, or implanted from the treatment probe, for the treatment of cancer for example.

In some embodiments, an image-guided treatment system comprises a treatment probe and an imaging probe. The imaging probe may be configured to provide an image of the target site while the treatment probe performs resection of the target tissue. The treatment probe and the imaging probe may each be coupled to robotic arms under control of one or more computing devices, in order to enable more precisely controlled movement of one or both of the arms and to improve the safety and efficiency of treatment using the treatment system.

FIG. 1 shows an exemplary embodiment of a system 400 for performing tissue resection in a patient. The system 400 may comprise a treatment probe 450 and an imaging probe 460. The treatment probe 450 may be coupled to a first arm 442, and the imaging probe 460 coupled to a second arm 444. One or both of the first arm 442 and the second arm 444 may comprise robotic arms whose movements may be controlled by one or more computing devices operably coupled with the arms. The treatment probe 450 may comprise a device for removing target tissue from a target site within a patient. The treatment probe 450 may be configured to deliver energy from the treatment probe 450 to the target tissue sufficient for removing the target tissue. For example, the treatment probe 450 may comprise an electrosurgical ablation device, a laser ablation device, a transurethral needle ablation device, a water jet ablation device, an ultrasound ablation transducer, or any combination thereof. The imaging probe 460 may be configured to deliver energy from the imaging probe 460 to the target tissue sufficient for imaging the target tissue. The imaging probe 460 may comprise an ultrasound probe, a magnetic resonance probe, an endoscope, or a fluoroscopy probe, for example. The first arm 442 and the second arm 444 may be configured to be independently adjustable, adjustable according to a fixed relationship, adjustable according to a user selected relationship, independently lockable, or simultaneously lockable, or any combination thereof. The first arm 442 and the second arm 444 may have multiple degrees of freedom, for example six degrees of freedom, to manipulate the treatment probe 450 and the imaging probe 460, respectively. The treatment system 400 may be used to perform tissue resection in an organ of a patient, such a prostate of a patient. The patient may be positioned on a patient support 449 such as a bed, a table, a chair, or a platform. The treatment probe 450 may be inserted into the target site of the patient along an axis of entry that coincides with the elongate axis 451 of the treatment probe. For example, the treatment probe 450 may be configured for insertion into the urethra of the patient, so as to position an energy delivery region of the treatment probe within the prostate of the patient. The imaging probe 460 may be inserted into the patient at the target site or at a site adjacent the target site of the patient, along an axis of entry that coincides with the elongate axis 461 of the imaging probe. For example, the imaging probe 460 may comprise a transrectal ultrasound (TRUS) probe, configured for insertion into the rectum of the patient to view the patient's prostate and the surrounding tissues. As shown in FIG. 1, the first arm 442 and the second arm 444 may be covered in sterile drapes to provide a sterile operating environment, keep the robotic arms clean, and reduce risks of damaging the robotic arms. Further details regarding the various components of the system 400 suitable for incorporation with embodiments as disclosed herein may be found in U.S. Pat. Nos. 7,882,841, 8,814,921, 9,364,251, and PCT Publication No. WO2013/130895, the entire disclosures of which are incorporated herein by reference.

Figure 2:
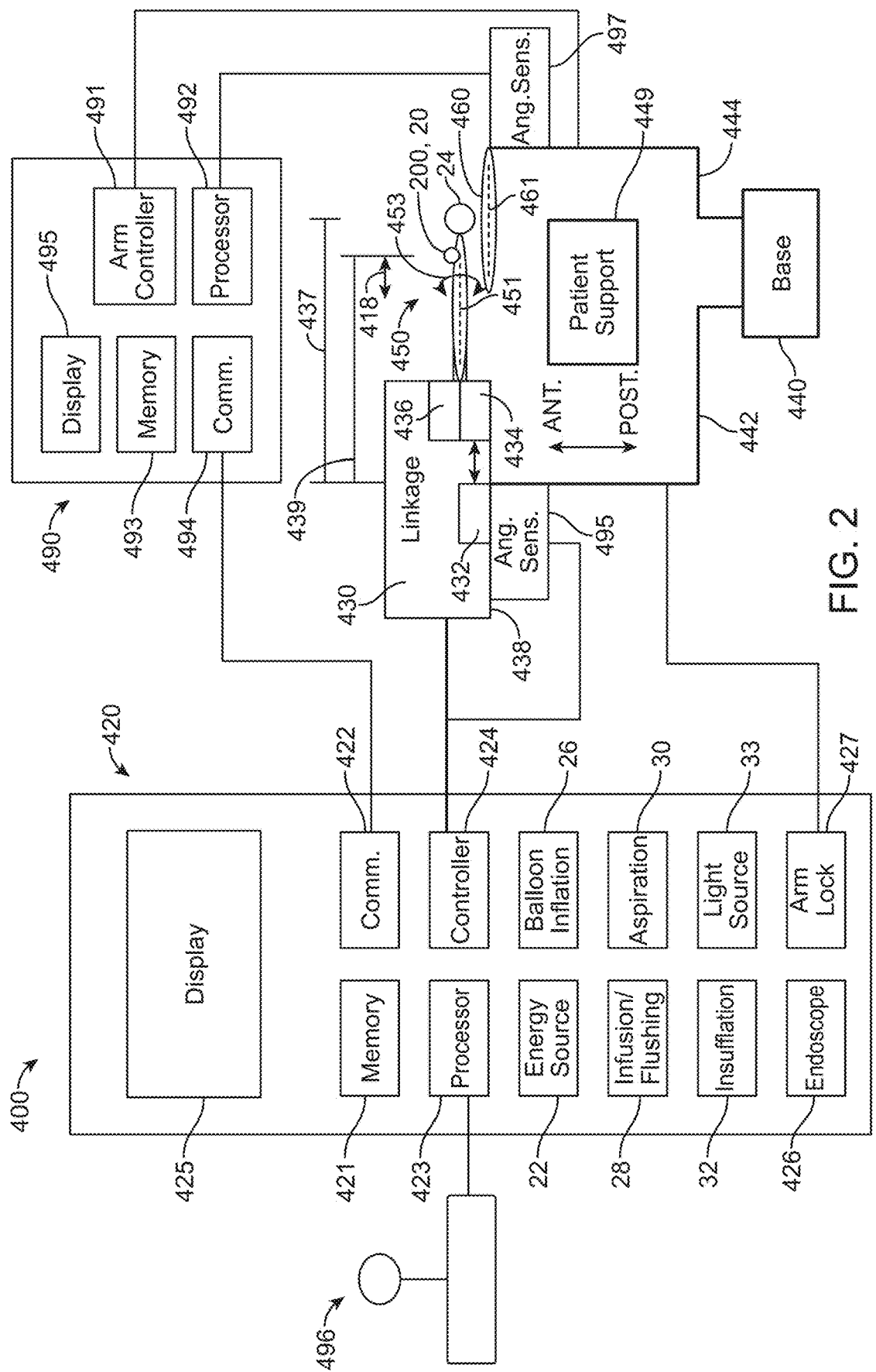
FIG. 2 schematically illustrates a system for performing tissue resection in a patient, in accordance with some embodiments.

FIG. 2 schematically illustrates an exemplary embodiment of the system 400 for performing tissue resection in a patient. The system 400 comprises a treatment probe 450 and may optionally comprise an imaging probe 460. The treatment probe 450 is coupled to a console 420 and a linkage 430. The linkage 430 may comprise one or more components of the robotic arm 442. The imaging probe 460 is coupled to an imaging console 490. The imaging probe may be coupled to the second robotic arm 444, for example. The patient treatment probe 450 and the imaging probe 460 can be coupled to a common base 440. The patient is supported with the patient support 449. The treatment probe 450 is coupled to the base 440 with a first arm 442. The imaging probe 460 is coupled to the base 440 with a second arm 444. One or both of the first arm 442 and the second arm 444 may comprise robotic arms whose movements may be controlled by one or more computing devices operably coupled with the arms, as described in further detail herein.

Although reference is made to a common base, the robotic arms can be coupled to a bed rail, a console, or any suitable supporting structure to support the base of the robotic arm.

In some embodiments, system 400 comprises a user input device 496 coupled to processor 423 for a user to manipulate the surgical instrument on the robotic arm. In some embodiments, the user input device comprises a controller to move the end of the treatment probe or the imaging probe with movements in response to mechanical movements of the user input device. The end of the probe can be shown on the display 425 and the user can manipulate the end of the probe. For example, the user input device may comprise a 6 degree of freedom input controller in which the user is able to move the input device with 6 degrees of freedom, and the distal end of the probe moves in response to movements of the controller. In some embodiments, the 6 degrees of freedom comprise three translational degrees of freedom and three rotational degrees of freedom. The processor can be configured with instructions for the probe control to switch between automated image guidance treatment with the energy source and treatment with the energy source with user movement of the user input device, for example.

The patient is placed on the patient support 449, such that the treatment probe 450 and ultrasound probe 460 can be inserted into the patient. The patient can be placed in one or more of many positions such as prone, supine, upright, or inclined, for example. In some embodiments, the patient is placed in a lithotomy position, and stirrups may be used, for example. In some embodiments, the treatment probe 450 is inserted into the patient in a first direction on a first side of the patient, and the imaging probe is inserted into to the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each of the first and second arms may comprise a substantially unlocked configuration such the treatment or imaging probe can be desirably rotated and translated in order to insert the probe into to the patient. When the probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image date of the imaging probe to treatment probe coordinate references. Having the tissue image data mapped to treatment probe coordinate reference space can allow accurate targeting and treatment of tissue identified for treatment by an operator such as the physician.

In some embodiments, the treatment probe 450 is coupled to the imaging probe 460 in order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In some embodiments, the first arm 442 is a movable and lockable arm such that the treatment probe 450 can be positioned in a desired location in a patient. When the probe 450 has been positioned in the desired location of the patient, the first arm 442 can be locked with an arm lock 427. The imaging probe can be coupled to base 440 with the second arm 444, which can be used to adjust the alignment of the imaging probe when the treatment probe is locked in position. The second arm 444 may comprise a lockable and movable arm under control of the imaging system or of the console and of the user interface, for example. The movable arm 444 may be micro-actuatable so that the imaging probe 440 can be adjusted with small movements, for example a millimeter or so in relation to the treatment probe 450.

In some embodiments, the treatment probe 450 and the imaging probe 460 are coupled to angle sensors so that the treatment can be controlled based on the alignment of the imaging probe 460 and the treatment probe 450. A first angle sensor 495 may be coupled to the treatment probe 450 with a support 438. A second angle sensor 497 may be coupled to the imaging probe 460. The angle sensors may comprise one or more of many types of angle sensors. For example, the angle sensors may comprise goniometers, accelerometers and combinations thereof. In some embodiments, the first angle sensor 495 comprises a 3-dimensional accelerometer to determine an orientation of the treatment probe 450 in three dimensions. In some embodiments, the second angle sensor 497 comprises a 3-dimensional accelerometer to determine an orientation of the imaging probe 460 in three dimensions. Alternatively or in combination, the first angle sensor 495 may comprise a goniometer to determine an angle of treatment probe 450 along an elongate axis 451 of the treatment probe. The second angle sensor 497 may comprise a goniometer to determine an angle of the imaging probe 460 along an elongate axis 461 of the imaging probe 460. The first angle sensor 495 is coupled to a controller 424 of the treatment console 420. The second angle sensor 497 of the imaging probe is coupled to a processor 492 of the imaging console 490. Alternatively or in combination, the second angle sensor 497 may be coupled to the controller 424 of the treatment console 420.

The console 420 comprises a display 425 coupled to a processor system and components that are used to control treatment probe 450. The console 420 comprises a processor 423 having a memory 421. Communication circuitry 422 is coupled to processor 423 and controller 422. Communication circuitry 422 is coupled to the imaging console 490 via the communication circuitry 494 of the imaging console. Arm lock 427 of console 420 may be coupled to the first arm 442 to lock the first arm or to allow the first arm to be freely movable to insert probe 450 into the patient.

Optionally, the console 420 may comprise components of an endoscope 426 that is coupled to anchor 24 of the treatment probe 450. Endoscope 426 can comprise components of console 420 and an endoscope insertable with treatment probe 450 to treat the patient.

Optionally, the console 420 may comprise one or more of modules operably coupled with the treatment probe 450 to control an aspect of the treatment with the treatment probe. For example, the console 420 may comprise one or more of an energy source 22 to provide energy to the treatment probe, balloon inflation control 26 to affect inflation of a balloon used to anchor the treatment probe at a target treatment site, infusion/flushing control 28 to control infusion and flushing of the probe, aspiration control 30 to control aspiration by the probe, insufflation control 32 to control insufflation of the target treatment site (e.g., the prostate), or a light source 33 such as a source of infrared, visible light or ultraviolet light to provide optical energy to the treatment probe.

The processor, controller and control electronics and circuitry can include one or more of many suitable components, such as one or more processor, one or more field-programmable gate array (FPGA), and one or more memory storage devices. In some embodiments, the control electronics controls the control panel of the graphic user interface (hereinafter "GUI") to provide for pre-procedure planning according to user specified treatment parameters as well as to provide user control over the surgery procedure.

The treatment probe 450 may comprise an anchor 24. The anchor 24 can anchor the distal end of the probe 450 while energy is delivered to energy delivery region 20 with the probe 450. The probe 450 may comprise a nozzle 200.

The treatment probe 450 may be coupled to the first arm 442 with a linkage 430. The linkage 430 may comprise components to move energy delivery region 20 to a desired target location of the patient, for example, based on images of the patient. The linkage 430 may comprise a first portion 432, a second portion 434 and a third portion 436. The first portion 432 may comprise a substantially fixed anchoring portion. The substantially fixed anchoring portion 432 may be fixed to support 438. Support 438 may comprise a reference frame of linkage 430. Support 438 may comprise a rigid chassis or frame or housing to rigidly and stiffly couple the first arm 442 to treatment probe 450. The first portion 432 can remain substantially fixed, while the second portion 434 and third portion 436 can move to direct energy from the probe 450 to the patient. The first portion 432 may be fixed to the substantially constant distance 437 to the anchor 24. The substantially fixed distance 437 between the anchor 24 and the fixed first portion 432 of the linkage allows the treatment to be accurately placed. The first portion 424 may comprise a linear actuator to accurately position the high-pressure nozzle 200 in the energy delivery region 20 at a desired axial position along an elongate axis 451 of treatment probe 450.

The elongate axis 451 of treatment probe 450 generally extends between a proximal portion of the probe 450 near linkage 430 to a distal end having anchor 24 attached thereto. The third portion 436 can control a rotation angle 453 around the elongate axis 451. During treatment of the patient, a distance 439 between the energy delivery region 20 and the first portion 432 of the linkage may vary with reference to anchor 24. The distance 439 may adjust in manner 418 in response to computer control to set a target location along the elongate axis 451 of the treatment probe referenced to anchor 24. The first portion of the linkage remains fixed, while the second portion 434 adjusts the position of the energy delivery region 20 along the axis 451. The third portion of the linkage 436 adjusts the angle 453 around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging console 490 may comprise a memory 493, communication circuitry 494 and processor 492. The processor 492 in corresponding circuitry is coupled to the imaging probe 460. An arm controller 491 is coupled to arm 444 to precisely position imaging probe 460. The imaging console may further comprise a display 425.

In order to facilitate precise control of the treatment probe and/or the imaging probe during treatment of the patient, each of the treatment probe and the imaging probe may be coupled to a robotic, computer-controllable arm. For example, referring to system 400 shown in FIG. 2, one or both of the first arm 442 coupled to the treatment probe 450 and the second arm 444 coupled to the imaging probe 460 may comprise robotic, computer-controllable arms. The robotic arms may be operably coupled with one or more computing devices configured to control movement of the robotic arms. For example, the first robotic arm 442 may be operably coupled with the processor 423 of the console 420, or the second robotic arm 444 may be operably coupled with the processor 492 of the imaging console 490 and/or to the processor 423 of the console 420. The one or more computing devices, such as the processors 423 and 492, may comprise computer executable instructions for controlling movement of the one or more robotic arms. The first and second robotic arms may be substantially similar in construction and function, or they may be different to accommodate specific functional requirements for controlling movement of the treatment probe versus the imaging probe.

The robotic arm may comprise 6 or 7 or more joints to allow the arm to move under computer control. Suitable robotic arms are commercially available from several manufacturers such as RoboDK Inc., Kinova Inc. and several other manufacturers.

The one or more computing devices operably coupled to the first and second robotic arms may be configured to automatically control the movement of the treatment probe and/or the imaging probe. For example, the robotic arms may be configured to automatically adjust the position and/or orientation of the treatment probe and/or imaging probe during treatment of the patient, according to one or more pre-programmed parameters. The robotic arms may be configured to automatically move the treatment probe and/or imaging probe along a pre-planned or programmed treatment or scanning profile, which may be stored on a memory of the one or more computing devices. Alternatively or additionally to automatic adjustment of the robotic arms, the one or more computing devices may be configured to control movement of the treatment probe and/or the imaging probe in response to user inputs, for example through a graphical user interface of the treatment apparatus. Alternatively or additionally to automatic adjustment of the robotic arms, the one or more computing devices may be configured to control movement of the treatment probe and/or the imaging probe in response to real-time positioning information, for example in response to anatomy recognized in one or more images captured by the imaging probe or other imaging source (from which allowable ranges of motion of the treatment probe and/or the imaging probe may be established) and/or position information of the treatment probe and/or imaging probe from one or more sensors coupled to the probes and/or robotic arms.

Figure 3B:
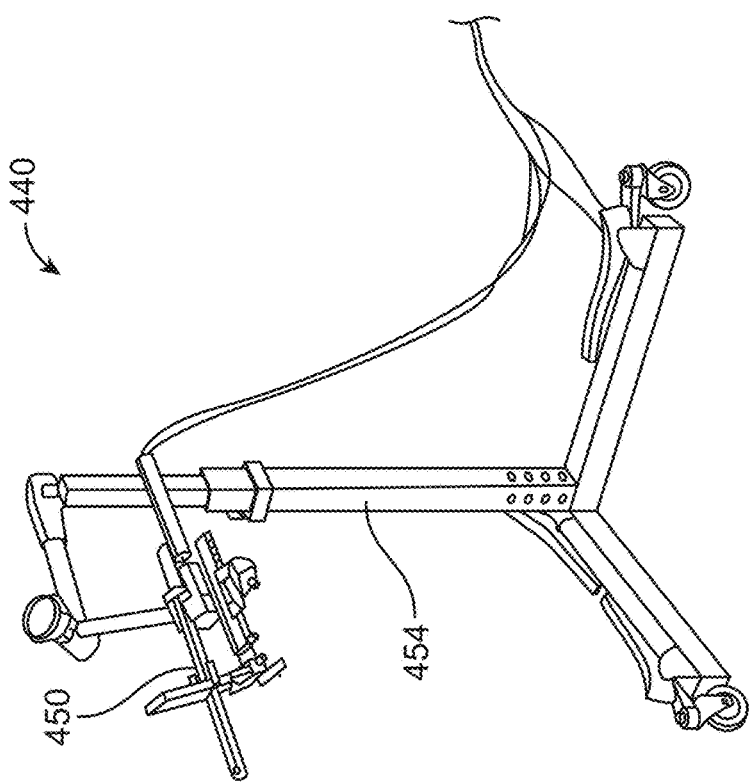
FIGS. 3A and 3B show perspective views of a common base or mount for supporting one or more robotic arms, in accordance with some embodiments.
Figure 3A:
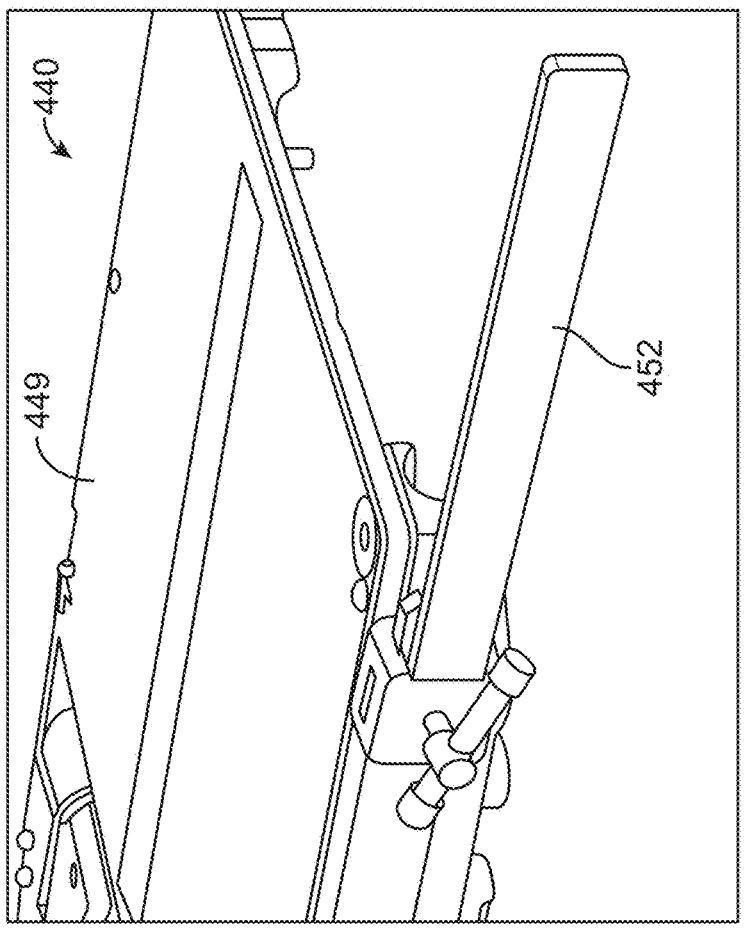

FIGS. 3A and 3B show exemplary embodiments of a common base or mount 440 for supporting one or more robotic arms of an image-guided treatment system as disclosed herein. FIG. 3A shows a patient support 449 comprising one or more rails 452. The patient support 449 may comprise a surgical table or a platform. One or more robotic arms associated with one or more of the treatment probe or the imaging probe may be mounted to the rails 452, such that the rails function as the common base 440. FIG. 3B shows a common base 440 comprising a floor stand 454 configured to couple to the first robotic arm connected to the treatment probe and/or the second robotic arm connected to the imaging probe. The floor-stand 454 may be positioned between the patient's legs during the treatment procedure.

Figure 4A:
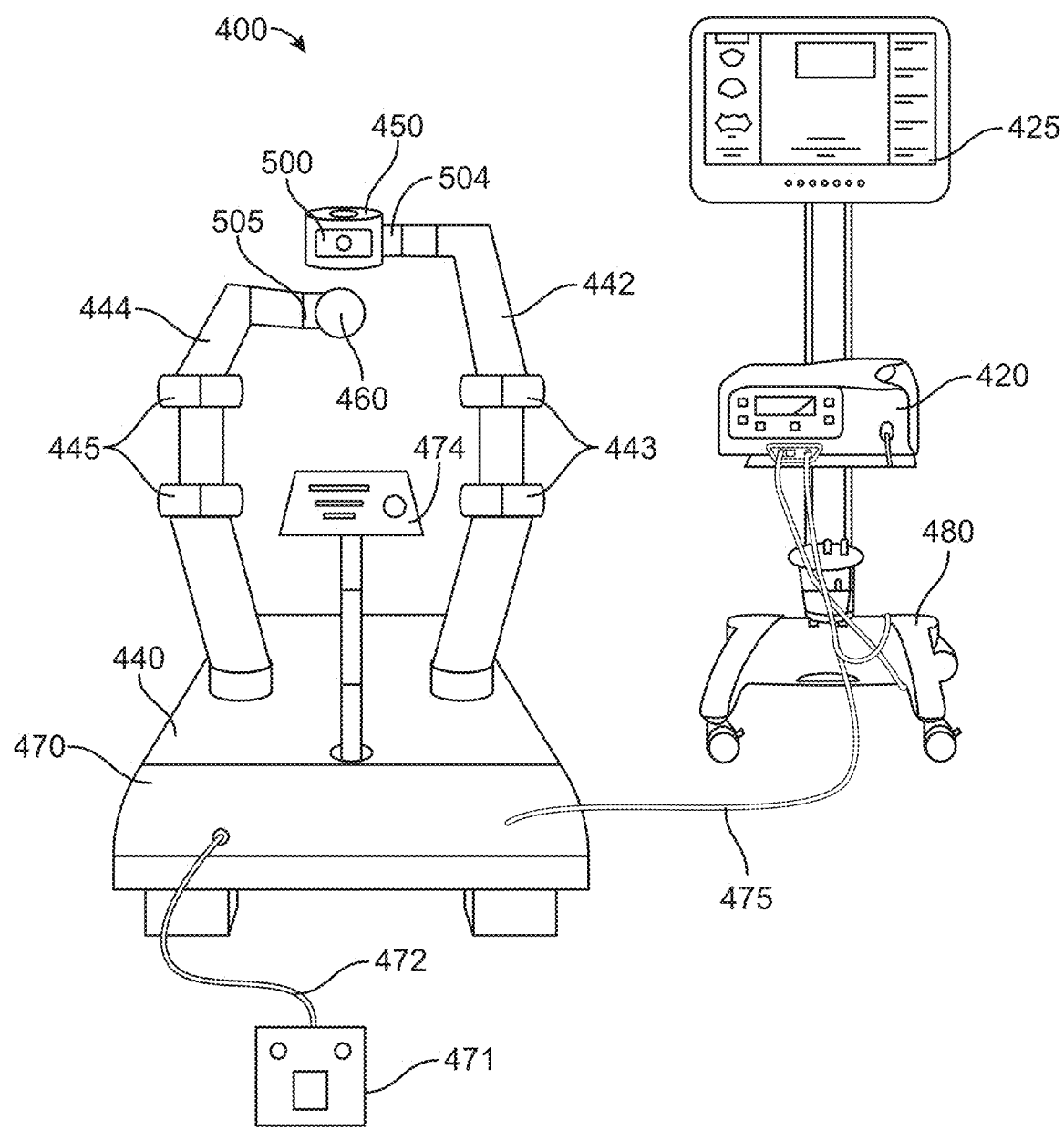
FIGS. 4A and 4B illustrate a perspective and side view, respectively, of a system for performing tissue resection in a patient that comprises a mobile base, in accordance with some embodiments.
Figure 4B:
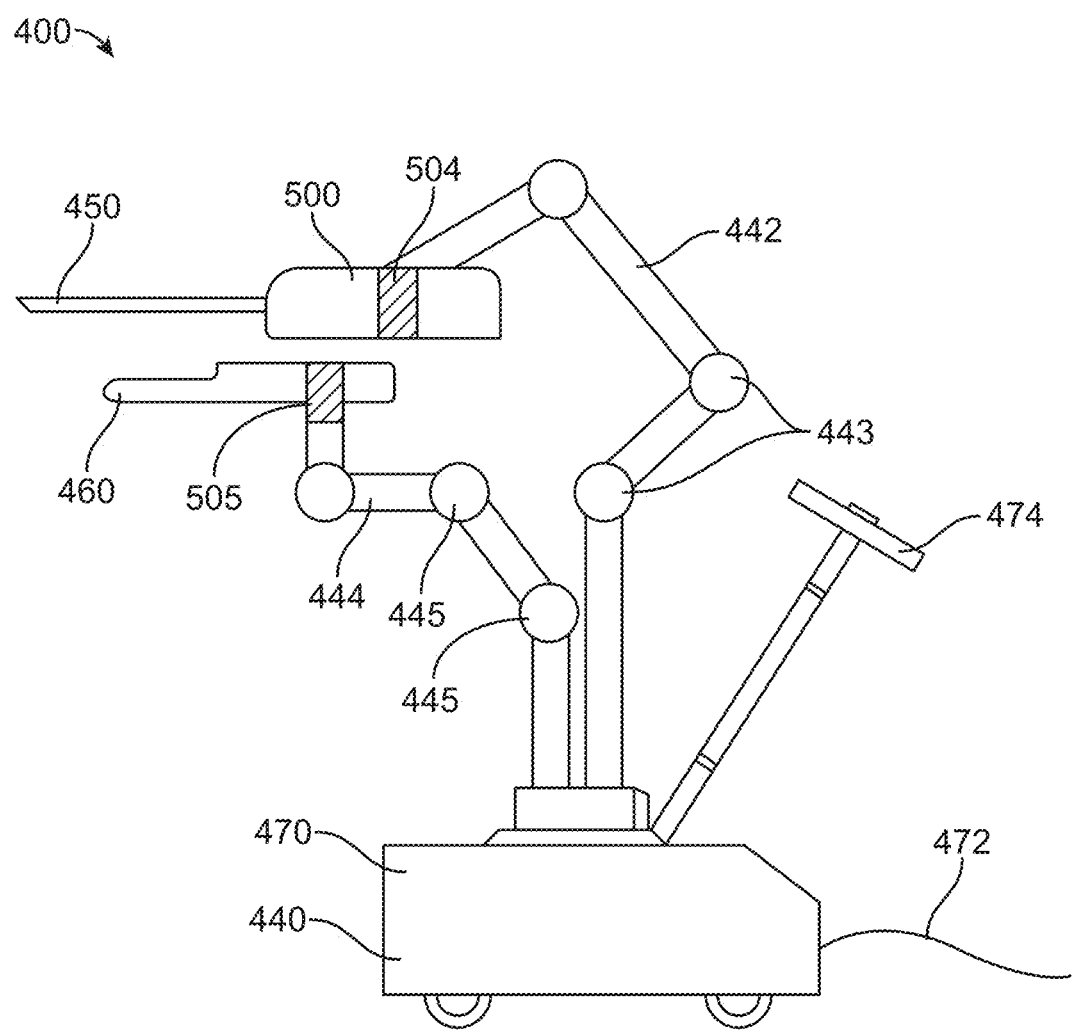

FIGS. 4A and 4B illustrate an exemplary embodiment of a treatment system 400 as described herein comprising a mobile base 470. FIG. 4A is a front view and FIG. 4B is a side view of the treatment system 400. The treatment system 400 comprises a treatment probe 450 coupled to a first robotic arm 442, and an imaging probe 460 coupled to a second robotic arm 444. The first robotic arm 442 and the second robotic arm 444 each comprises a proximal end and a distal end, the distal end coupled to the treatment probe 450 and the imaging probe 460, respectively, and the proximal end coupled to a common base 440 comprising a mobile base 470. The first robotic arm 442 may comprise a first arm coupling structure 504 to couple to the treatment probe 450, and the second robotic arm 442 may comprise a second arm coupling structure 505 to couple to the imaging probe 460. The treatment probe 450 may be coupled to the distal end of the first robotic arm 442 via an attachment device 500, which may comprise a linkage configured to effect movement of the treatment probe as described herein (e.g., rotation, translation, pitch, etc.). Coupling of the treatment probe 450 to the first robotic arm 442 may be fixed, releasable, or user adjustable. Similarly, coupling of the imaging probe 460 to the second robotic arm 444 may be fixed, releasable, or user adjustable.

The first robotic arm 442 may articulate at one or more first arm joints 443. The imaging arm 444 may articulate at one or more second arm joints 445. Each arm joint 443 or 445 may be operably coupled with a computer-controllable actuator, such as a step motor, to affect movement at the joint. Each arm joint 443 or 445 may comprise one of a variety of kinematic joints including but not limited to a prismatic, revolute, parallel cylindrical, cylindrical, spherical, planar, edge slider, cylindrical slider, point slider, spherical slider, or crossed cylindrical joint, or any combination thereof. Moreover, each arm joint 443 or 445 may comprise a linear, orthogonal, rotational, twisting, or revolving joint, or any combination thereof.

The system 400 may further comprise a console 420 as described herein, which may be supported by a mobile support 480 separate from the mobile base 470. The console 420 may be operably coupled with the mobile base 470 via a power and communication cable 475, to allow control of the treatment probe 450 coupled to the mobile base via the first robotic arm. The treatment console 420 comprises a processor and a memory having stored thereon computer-executable instructions for execution by the processor, to control various modules or functionalities of the treatment console, such as an energy source, infusion/flushing control, aspiration control, and other components as described herein with reference to FIG. 2. The treatment console 420 may further comprise a display 425 in communication with the processor. The display 425 may be configured to display, for example, one or more of: subject vital signs such as heart rate, respiratory rate, temperature, blood pressure, oxygen saturation, or any physiological parameter or any combination thereof; status of a procedure; one or more previously taken images or sequence of images of a treatment site from one or more views; one or more real-time images or sequence of images of the treatment site from one or more views acquired by the imaging probe 460; a set of treatment parameters including but not limited to a treatment mode such as cutting or coagulating, an intensity of treatment, time elapsed during treatment, time remaining during treatment, a depth of treatment, an area or volume of the treatment site that has been treated, an area of the treatment site that will be treated, an area or volume of the treatment site that will not be treated, location information of the treatment probe 450 or the imaging probe 460 or both; treatment adjustment controls such as means to adjust the depth of treatment, the intensity of treatment, the location and/or orientation of the treatment probe 450, the depth of imaging, or the location and/or orientation of the imaging probe 460, or any combination thereof; or system configuration parameters.

The mobile base 470 may further comprise one or more computing devices to control operation of the one or more robotic arms. For example, the mobile base may comprise processors and a memory having stored thereon computer executable instructions for execution by the one or more processors. The memory may have stored thereon instructions for operating the one or more robotic arms coupled to the mobile base. The processor may be operably coupled with the robotic arms via suitable electromechanical components to affect movement of the robotic arms. For example, each of the one or more joints of a robotic arm may comprise a step motor, and the processor may be operably coupled with the step motor at each joint to actuate the motor by a specified increment in a specified direction. Alternatively, the one or more robotic arms may be operably coupled with one or more processors of the console 420 or a separate imaging console (such as imaging console 490 shown in FIG. 2), wherein the one or more console processors may be configured to execute instructions for controlling movement of the one or more robotic arms, and may communicate the instructions to the robotic arms via communication circuitry (such as communication circuitry 422 of console 420 or communication circuitry 494 of console 490 shown in FIG. 2). The computer executable instructions for controlling movement of the robotic arms may be pre-programmed and stored on a memory, or may be provided by a user via one or more user inputs before or during treatment of the patient using the treatment system.

The one or more computing devices operably coupled with the first and/or second robotic arms may be configured to control movement of the arms so as to adjust the pitch, yaw, roll, and/or linear position of the treatment probe and/or imaging probe along the target site.

The mobile base 470 may comprise one or more user input devices to enable a user to control movement of the robotic arms under computer instructions. For example, as shown in FIGS. 4A and 4B, the mobile base may comprise a keyboard 474 and/or a footswitch 471, the footswitch operably coupled with the mobile base via a footswitch cable 472. The keyboard 474 and the footswitch 471, independently or in combination, may be configured to control operation of the first robotic arm 442 and/or the second robotic arm 444, for example via articulation of one or both robotic arms at one or more joints. The keyboard and the footswitch may be in communication with the one or more processors configured to control movement of the robotic arms. When a user inputs instructions into the keyboard and/or the footswitch, the user instructions can be received by the one or more processors, converted into electrical signals, and the electrical signals may be transmitted to the one or more computer-controllable actuators operably coupled with the one or more robotic arms. The keyboard and/or the footswitch may control movement of one or both arms towards or away from a treatment position, a position of interest, a predetermined location, or a user-specified location, or any combination thereof.

Optionally, the keyboard 474 and the footswitch 471, independently or in combination, may be configured to control operation of the treatment probe 450 and/or imaging probe 460. For example, the keyboard 474 and/or footswitch 471 may be configured to start, stop, pause, or resume treatment with the treatment probe. The keyboard 474 and/or footswitch 471 may be configured to begin imaging or freeze, save, or display on the display 425 an image or sequence of images previously or currently acquired by the imaging probe.

The mobile base 470 and the mobile support 480 of the console 420 may be independently positionable around a patient, supported by a patient support 449 such as a platform. For example, the mobile base 470, supporting the first and second robotic arms and the treatment and imaging probes, may be positioned between the patient's legs, while the mobile support 480 carrying the console 420 and the display 425 may be positioned to the side of the patient, such as near the torso of the patient. The mobile base 470 or the mobile support 480 may comprise one or more movable elements that enable the base or the support to move, such as a plurality of wheels. The mobile base 470 may be covered with sterile draping throughout the treatment procedure, in order to prevent contamination and fluid ingress.

Figure 5A:
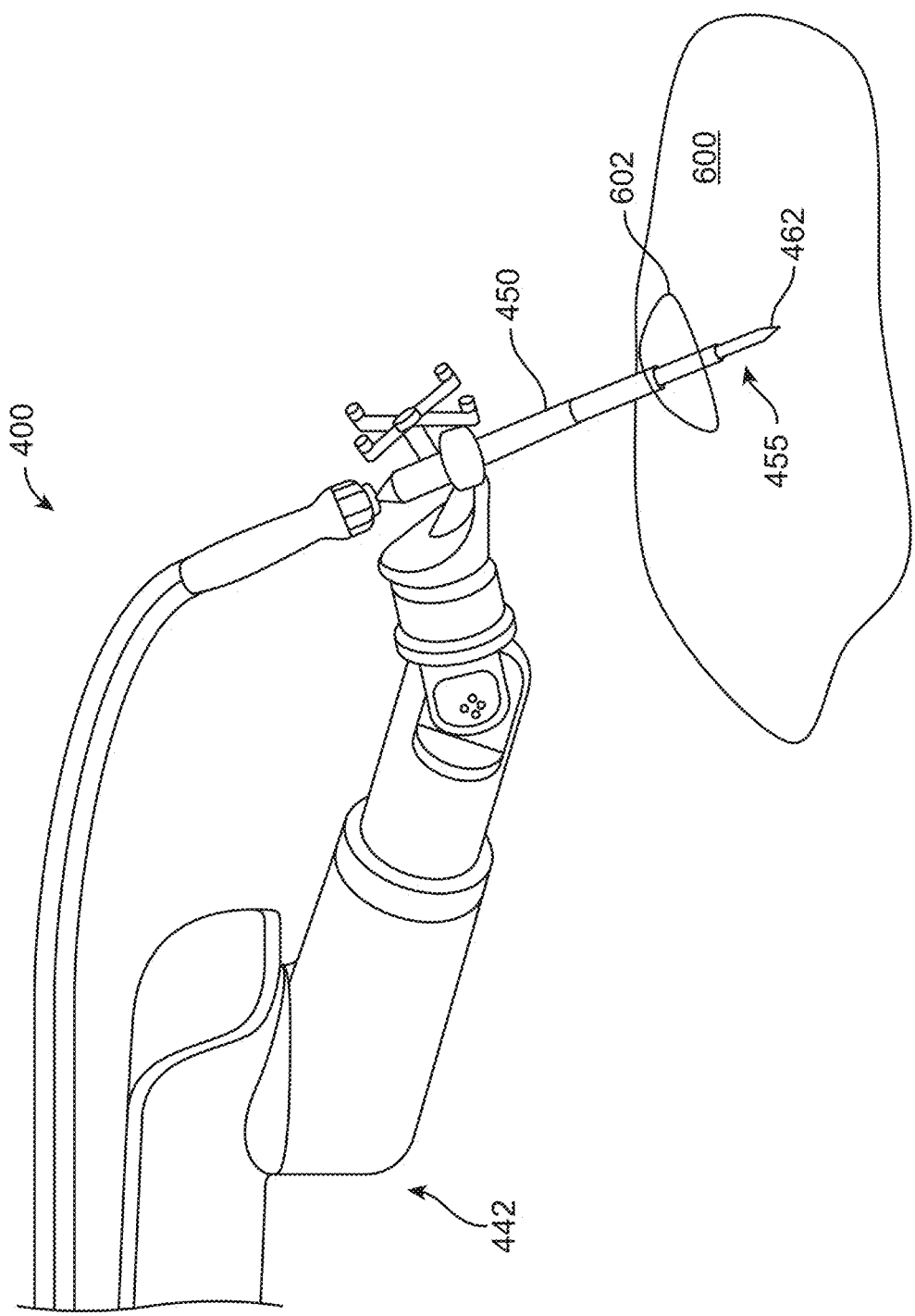
FIG. 5A shows a treatment probe coupled to a robotic arm in which the distal end of the robotic arm is configured to move the proximal end of the treatment probe with 6 degrees of freedom, in accordance with some embodiments.

FIG. 5A shows the treatment probe 450 coupled to the robotic arm 442 in which the distal end of the robotic arm is configured to move the proximal end of the treatment probe as described herein with 6 degrees of freedom. The treatment probe 450 and the robotic arm 400 may comprise one or more components of system 400 as described herein. These movements of the proximal end of the probe correspond to movements of the energy source 455 near the distal end of the probe. In some embodiments, the robotic arm comprises 6 degrees of freedom, the probe is moved in accordance with instructions from the processor, which may comprise instructions of a programmed treatment plan or in response to user input controls. The probe tip 462 can be moved to a plurality of locations to resect tissue 600 with movements of robotic arm 442. In some embodiments, an enclosure 602 is placed over the resected tissue 600 to provide a beneficial fluidic environment to the tissue 600 for tissue resection. Alternatively, the probe tip 462 can be inserted through an opening into the patient to a recess within the patient such as an organ 608 as described herein, which can provide a beneficial fluidic environment. In some embodiments, the probe comprises a stiff probe, which allows the position of the tip 462 of the probe to be accurately positioned and oriented in response to the position and orientation of the distal end of the robotic arm. Alternatively, the probe may comprise a flexible probe, in which at least a portion of the probe is flexible. The energy source 455 near the tip 462 of the treatment probe 450 may comprise any energy source 455 as described herein.

The tissue access site can be accessed in one or more of many ways, for example, with open surgical access through an incision, an access through a small incision, or with insertion through an external opening of a body lumen such as the urethra. The access may comprise access for an open prostatectomy or an open nephrectomy, for example.

The enclosure 602 may comprise any suitable barrier material that allows an appropriate environment to be provided to the tissue 600, such as a plastic, silicone, or other material. In some embodiments, the enclosure 602 comprises a flexible material that can deform and contour to the surface of the tissue 600 upon which it has been placed.

Figure 5B:
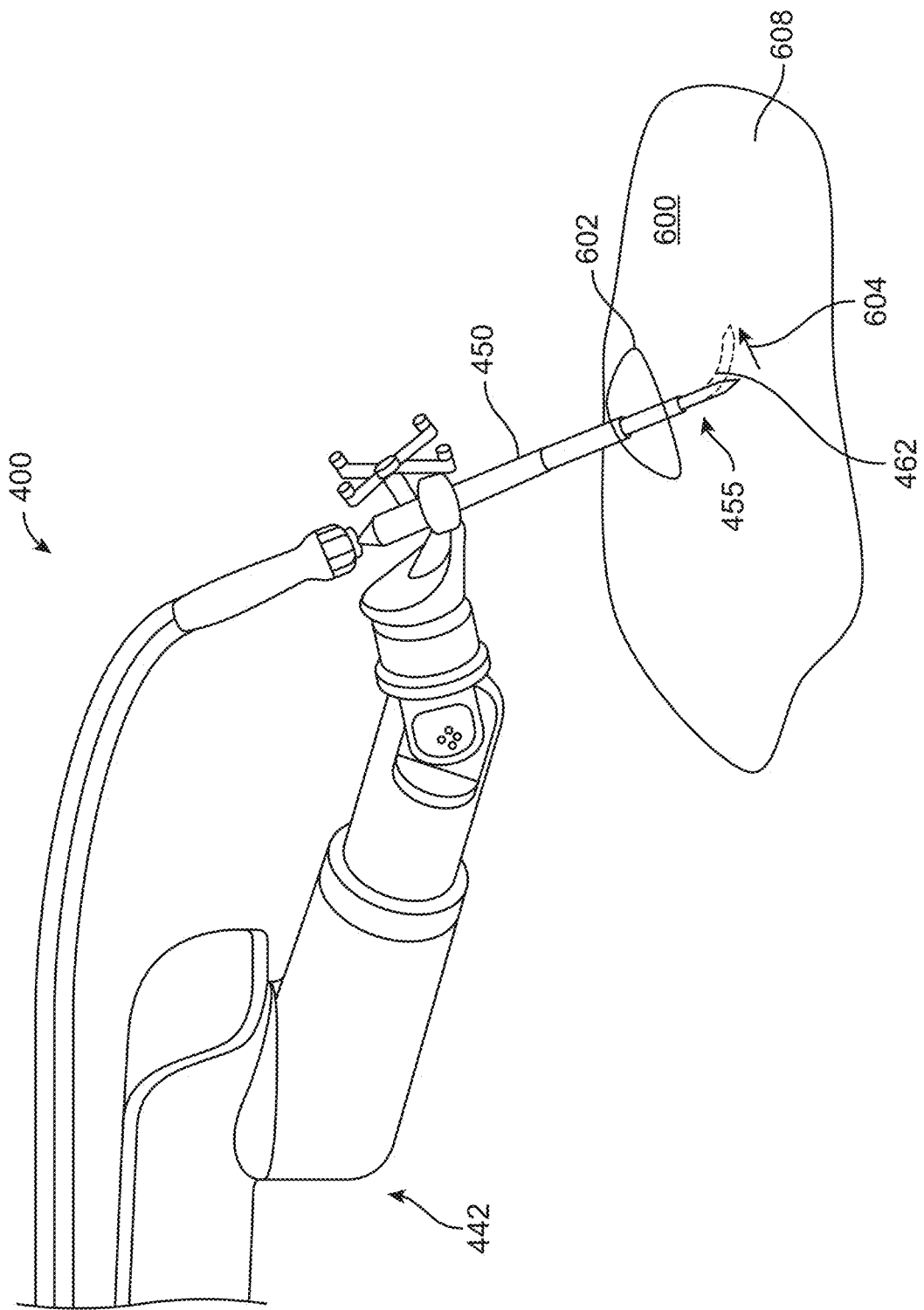
FIG. 5B shows a treatment probe coupled to a robotic arm as in FIG. 5A, in which the distal end portion of the treatment probe comprises a deflectable tip, in accordance with some embodiments.

FIG. 5B shows a treatment probe 450 coupled to a robotic arm 442 as in FIG. 5A, in which the distal end portion of the treatment probe comprises a deflectable tip 462. The treatment probe 450 and the robotic arm 400 may comprise one or more components of system 400 as described herein. The deflectable tip 462 can be configured in many ways. For example, the deflectable tip 462 may comprise a flexible elongate tubular member that can bend and deflect in response to an internal lumen of the patient. In some embodiments, the deflectable tip 462 comprises a controllable tip in which the amount of deflection 604 can be controlled in response to instructions. For example, the tip 462 may comprise pull wires or other elongate elements that allow the angle of deflection to be controlled, for example in response to one or more of the processor, the user interface, or the user input device. In some embodiments, the probe comprises a stiff probe when deflected to a controlled position. The treatment probe 450 can be configured to rotate about an elongate axis of the probe in combination with the movement of the end of the robotic arm as described herein, in order to direct energy to a targeted tissue location. In some embodiments, the probe is configured to deflect the distal end, in order to direct the energy to targeted tissue location with rotation of the probe about the elongate axis of the probe. In some embodiments, the probe comprises a stiff deflection in order to resist forces from a water jet emitted from the probe. In some embodiments, the probe comprises a plurality of openings, in which one opening is directed toward tissue and another water jet is oriented in an opposite direction, e.g. toward a shield, to provide an opposing force to the force of the water jet.

Figure 5C:
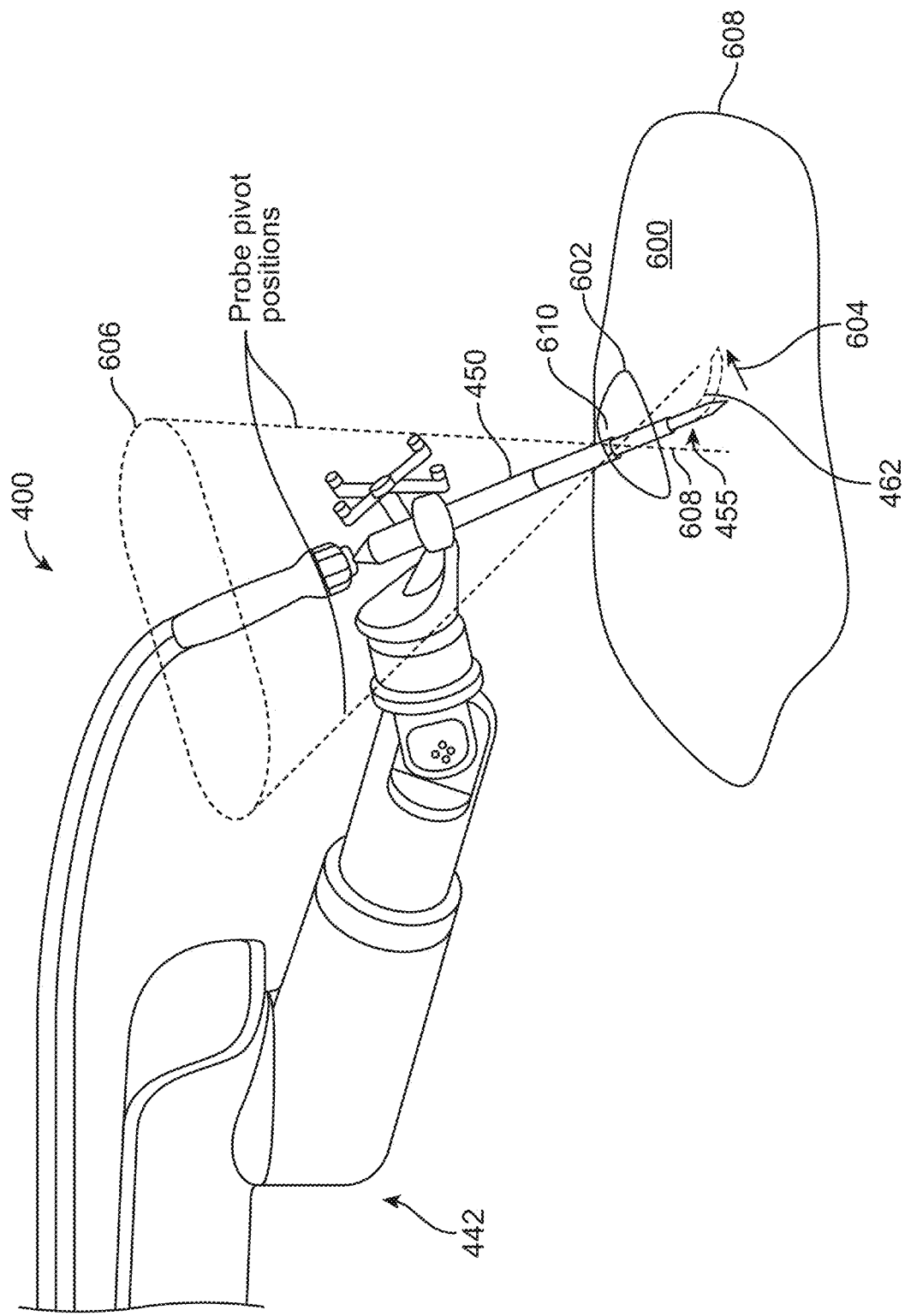
FIG. 5C shows probe pivoting about a location, in accordance with some embodiments.

FIG. 5C shows probe pivoting of the treatment probe 450 about a location 610. The processor can be configured with instructions to pivot the probe 450 about a pivot location 610, which may comprise any suitable location. For example, the pivot location 610 may correspond to an opening of an enclosure or an opening to an internal body lumen. In some embodiments, the pivot location 610 is near a verumontanum of the patient, near an external sphincter of the urethra, or in between the verumontanum and the external sphincter. Alternatively or in combination, in some embodiments the pivot location 610 of the surgical corresponds to the pubic bone.

While the pivoting movement can be configured in many ways, the pivoting movement can be confiture to move the proximal end of the probe along a path 606, so as to move the tip 462 of the probe along a corresponding path to direct energy to the targeted tissue location. The path 606 of the proximal end may define an enclosed volume and the path 608 of the distal end may define an enclosed volume around a tissue 600 to be removed in order to isolate the tissue 600 to be removed from surrounding tissue, such as the organ 608. For example, the treatment probe may pivot about the pivot location 610 while benign prostate hyperplasia is removed from an organ, such as the prostate, with the energy source 455 located within the prostate capsule. Because tissue near the end of the external opening of the urethra is typically flexible near the open end of the urethra, the tissue near the open end of the urethra can move similarly to the proximal end of the probe with the pivot 610 between the proximal end of the urethra and the distal end of the probe. In some embodiments, the tissue treatment area, e.g. prostate, is scanned with a scan pattern and the external opening to the urethra moves in a corresponding pattern with the pivot 610 therebetween.

The deflectable tip 462 of the probe can be used in many ways. For example, the flexible probe tip 462 can be used to separate capsular tissue from glandular tissue with the energy source 455, such as a laser energy source as described herein. In some embodiments, the deflectable probe tip 462 can be used to separate glandular tissue from capsular tissue, for example to separate the capsule of the prostate from the glandular tissue of the prostate. In some embodiments, the probe tip 462 deflects in response to increased resistance of the capsule to movement compared with the resistance of the glandular tissue. In some embodiments, the probe tip 462 can be controlled by the system operator to move along an interior boundary of the capsule to separate the capsule from the glandular prostate tissue. Work in relation to embodiments, suggests that the capsular tissue is loosely connected to the glandular tissue along an interface between the capsule and the glandular tissue, such that the capsular tissue can be separated from the glandular tissue with mechanical force along the interior of the capsular tissue. In some embodiments, the deflectable tip 462 is configured to deflect under user control, for example with elongate elements extending along the deflectable tip 462, so that the user can control the amount of deflection 604. The deflectable probe tip 462 may comprise an energy source 455 as described herein or may transmit mechanical energy to the tip 462 with movement of the tip 462 so as to separate the capsular tissue from the glandular tissue.

In some embodiments, the probe 450 is placed on the capsule of the organ 608 to be resected and tensioned, so as to facilitate separation of the capsule from glandular tissue.

Figure 6:
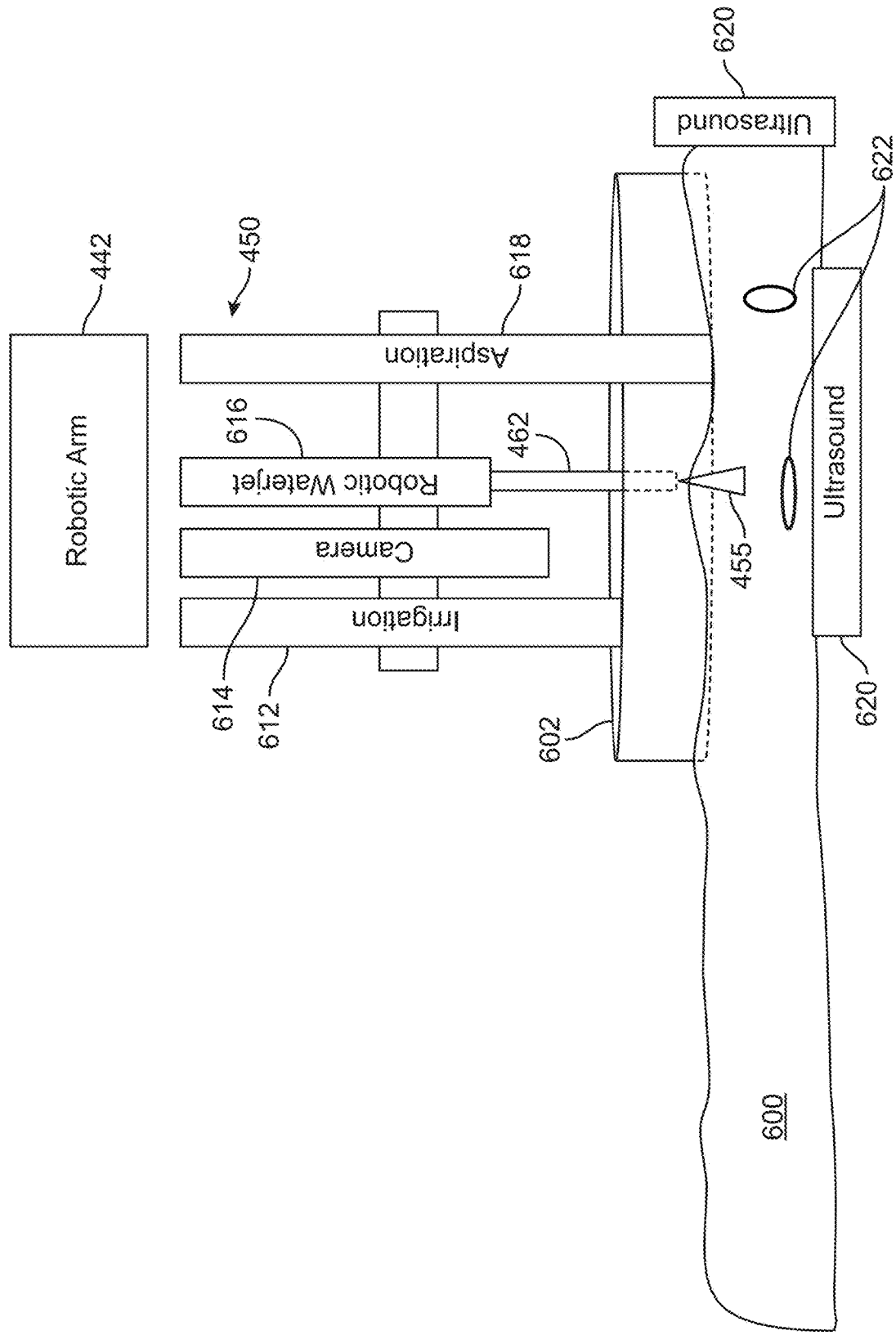
FIG. 6 shows a treatment probe coupled to the distal end of the robotic arm, in which the treatment probe comprises one or more of irrigation, aspiration, a robotic energy source, or a camera, in accordance with some embodiments.

FIG. 6 shows a treatment probe 450 coupled to the distal end of the robotic arm as in FIG. 5. The treatment probe comprises one or more of a fluid delivery lumen, such as irrigation lumen 612, and delivery port, an endoscopic 614, such as the camera, for viewing the surgical site, an energy delivery channel, such as the robotic water jet device, and an energy source 455, such as a water jet, and an aspiration lumen 618. The probe may comprise an elongate probe and can extend a distance within a range from about 5 cm to about 50 cm from the proximal end of the probe to the distal end of the probe. The enclosure can be placed over a tissue to fluidically isolate the tissue to create an environment beneficial for tissue resection. For example, the fluid delivery lumen 612 can be connected to source of fluid, such as a gas, e.g. $CO_2$, or a liquid, e.g. water or saline. In some embodiments, the energy source 455 comprises a water jet that is emitted from the end of the probe. For example, the energy source 455 can direct energy aligned coaxially with an axis of the of the energy delivery channel, for example straight out the end of the energy delivery channel. The energy deliver channel may comprise any suitable structure for delivering energy, such as one or more optical fibers to deliver light energy, a tube to deliver water jet energy, wires for electrical energy or cautery or ultrasonic energy to the treatment site.

In some embodiments, the treatment probe 450 comprises a substantially straight stiff probe with the water jet emitted from the end of the probe. The water jet 455 can be scanned to selectively resect tissue in response to movement of the robotic arm. For example, the robotic arm can 442 be configured to move the distal end of the probe with the scan pattern by moving the proximal end of the probe coupled to the robotic arm. Although reference is made to a robotic arm with 6 degrees of freedom, the robotic arm may comprise fewer degrees of freedom, for example three translational degrees of freedom to move water jet from the probe in a scanning pattern.

In some embodiments, one or more ultrasound probes 620 are coupled to the tissue 600. For example, the one or more ultrasound probes 620 may comprise external ultrasound probes coupled to the tissue 600 through a skin of the patient. Alternatively, the one or more ultrasound probes 600 may comprise a probe inserted into the patient. The ultrasound probes 600 can be configured to provide three-dimensional imaging, for example.

In some embodiments, one or more imaging markers 622 can be placed on the tissue 600 in order to track movement of the tissue 600 and maintain alignment of the treatment probe 620 with the target tissue.

In some embodiments, a contrast agent is injected into a blood vessel such as an artery in order to improve imaging of one or more of the tissue or the blood vessels.

In some embodiments, the robotic arm 442 and probe 450 are configured to provide positional accuracy of the tip 462 of the probe and energy source 455 to within a desired tolerance, for example to within about 2 mm of an intended target position of the end of the probe.

FIG. 7A shows a tissue resection profile 700 to resect tissue to a depth with a first removal layer. The tissue resection profile 700 can be generated with instructions on the processor to move the tissue in a scanning pattern 702 by moving the proximal end of the robotic arm to move the tip of the probe and water jet to appropriate locations to scan the tissue with the scan pattern 702.

FIG. 7B shows a tissue resection profile 700 to remove tissue 600 away from an undesirable tissue such as a tumor, which may comprise a cancerous or benign tumor. Work in relation to the present disclosure suggests that it may be helpful to resect tissue around a boundary of the tumor so as to leave the tumor substantially intact. Other undesirable tissues can be removed similarly such as cirrhotic tissue or other tissues as described herein. The tissue resection profile 700 can be generated with instructions on the processor to move the tissue in a scanning pattern 702 by moving the proximal end of the robotic arm to move the tip of the probe and water jet to appropriate locations about the resection boundary 704. Once the tissue 600 has been resected around the resection boundary 704 to decouple the tumor from healthy tissue, the undesirable can be removed. Although FIG. 7B illustrates tissue resection along a layer of resection, in some embodiments tissue is sequentially resected with a plurality of removal layers. For example, a first layer can be removed with tissue resected up to the resection boundary 600, and a second removal layer resected up to a second removal boundary. For 3D tissue resection, a plurality of removal layers and boundaries 600 can be defined, so as to remove tissue along a 3D boundary with a 3D tissue rejection profile.

FIG. 7C shows a 3D tissue resection profile 700 around a tumor to remove tissue away from the tumor. The probe on the robotic arm can be scanned with a 3D scan pattern 702 in response to instructions from the processor. For example, the proximal end of the probe can be moved with five or six degrees of freedom by moving the robotic arm accordingly to direct the energy source such as a water jet to the target tissue site. In some embodiments, the water jet is directed out the end of the probe aligned with the axis of the probe, e.g. substantially straight. The proximal end of the probe can be translated and rotate to provide resection along the three-dimensional tissue resection boundary 704. In some embodiments, the tissue 600 can be resected in a plurality of layers of substantially equal depth, in which the probe removes each subsequent layer after the tissue has been resected along the boundary for a prior layer. The angle of the elongate axis of the probe can be inclined at various angles along the tissue resection boundary 704 so as to decrease movement of the tissue with the probe as the probe is inserted further into the tissue along the boundary 704, for example.

FIG. 7D shows a conical tissue resection profile 700 to remove tissue 600 away from a tumor. The probe can be moved and oriented along a scan pattern 702 to direct the energy source, e.g. water jet along the tissue resection boundary 704. For example, the probe can be moved in a movement direction 630 to a plurality of positions and orientations 640 corresponding to a frustrum of a cone 632, so as to resect the conic resection boundary 704 with the energy source, e.g. water jet.

Figure 8:
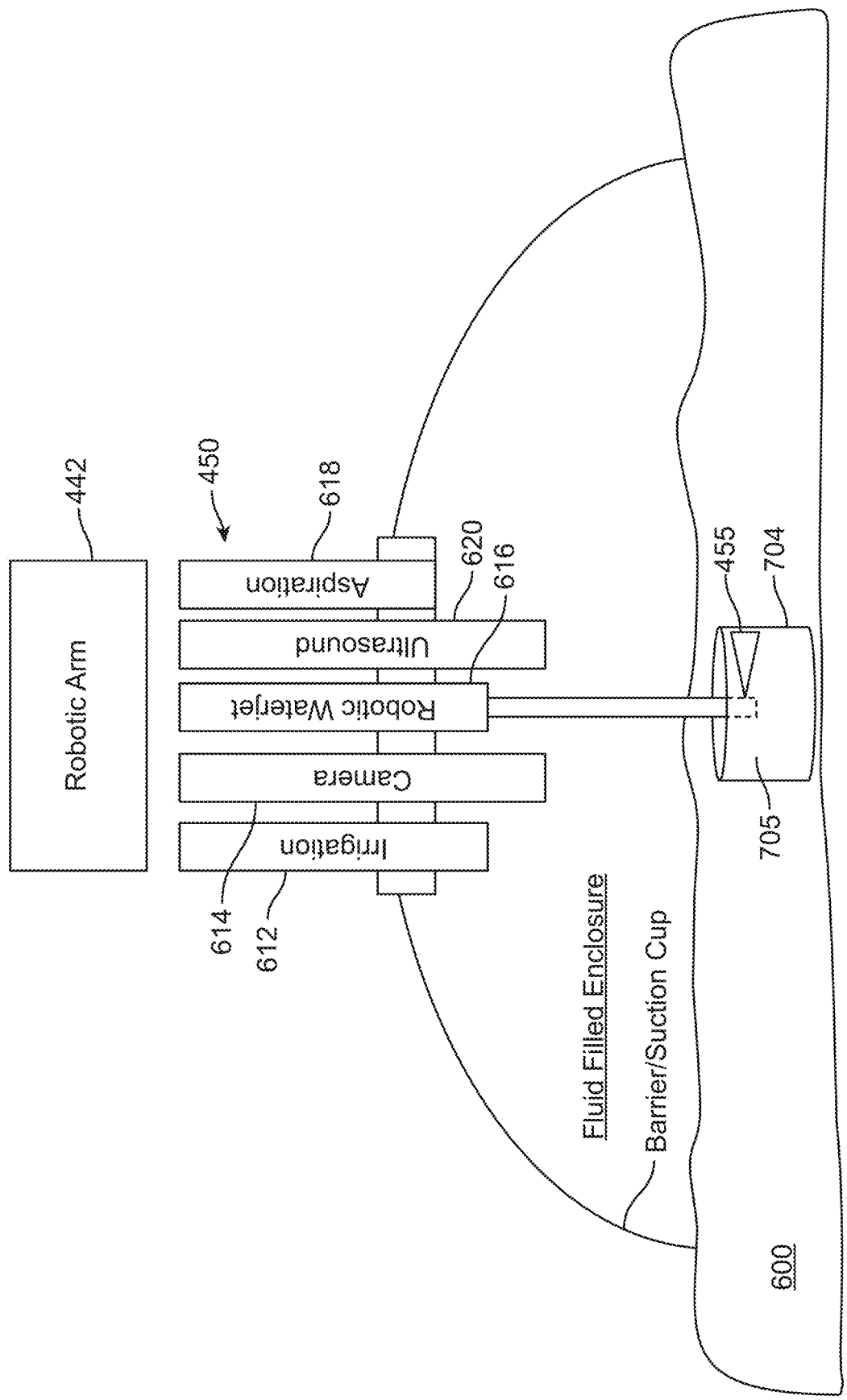
FIG. 8 shows a treatment probe comprising a rotating energy source coupled to the distal end of a robotic arm as in FIG. 5, in accordance with some embodiments.

FIG. 8 shows a treatment probe 450 comprising a rotating energy source 455, such as a water jet, coupled to the distal end of a robotic arm 442. The probe comprises one or more components of probe 450 as described herein with reference to FIG. 5. In some embodiments, the probe comprises an ultrasonic imaging transducer 620 to image the tissue resection with the energy source, such as the water jet. In some embodiments, the energy source 455 is configured to move independently relative to the end of the robotic arm, for example with one or more of rotation, translation, rotational oscillation or translational oscillation of the energy source relative to the tissue and the end of the robotic arm.

In some embodiments, an enclosure 602 is placed over the resected tissue 600 to provide a beneficial fluidic environment to the tissue 600 for tissue resection. The enclosure 602 may comprise any suitable barrier material that allows an appropriate environment to be provided to the tissue 600, such as a plastic, silicone, or other material. In some embodiments, the enclosure 602 comprises a flexible material that can deform and contour to the surface of the tissue 600 upon which it has been placed. In some embodiments, the barrier may be a cup or suction cup.

FIGS. 9 to 12B show a method of tissue resection with a water jet with a robotic arm. In some embodiments, tissue is resected into a plurality of resection layers sequentially with scanning of the water jet at each of the plurality of layers.

Figure 9:
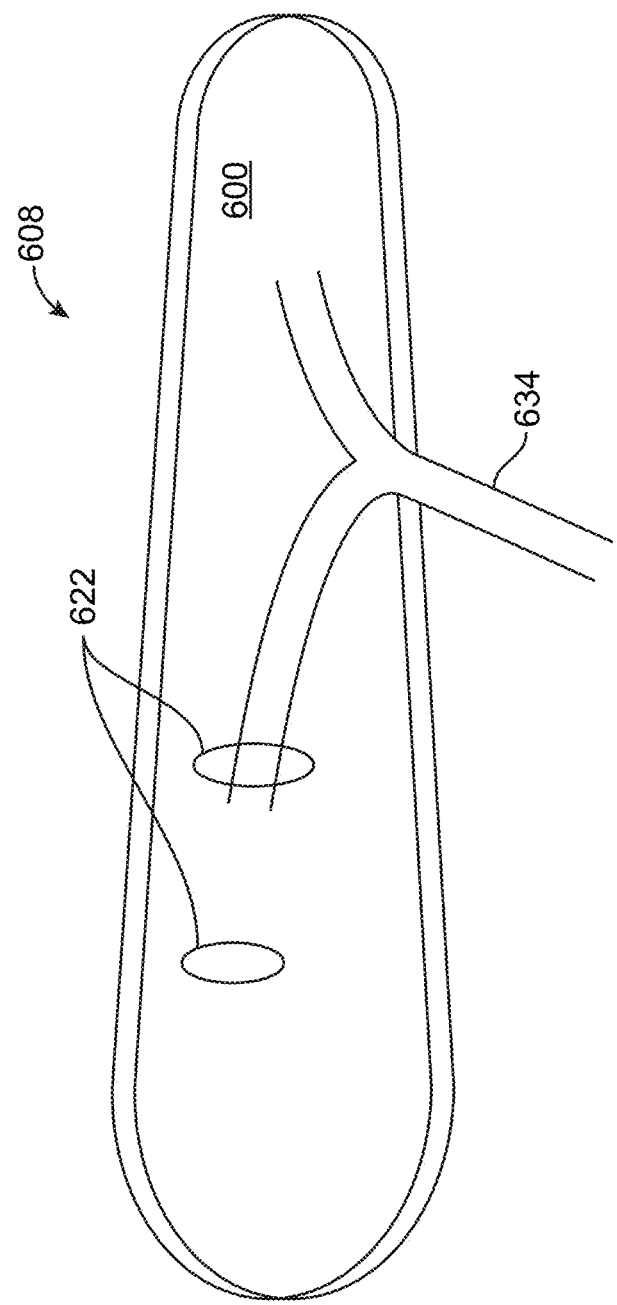

At a step shown in FIG. 9, the tissue 600, such as parenchymal tissue, of an organ 608 is visualized, for example with imaging as described herein, such as with one or more of an endoscope, ultrasonic imaging, ultrasound, MRI or CT scan imaging. The imaging may include visualizing of a neuro vascular bundle, vein, or blood vessel 634. In some embodiments one or more markers 622 are placed on the tissue 600 to identify movement of the tissue and to register the treatment with the tissue.

Figure 10:
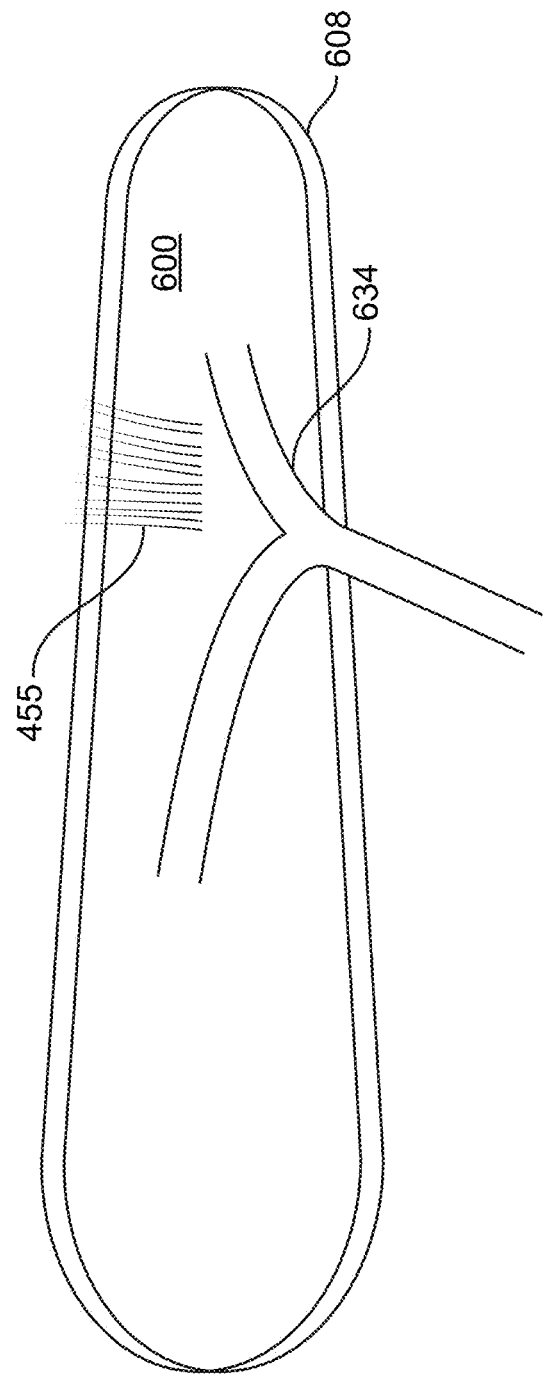

At a step as shown in FIG. 10 tissue resection with energy from the energy source 455 is initiated to resect a first layer of tissue 600, such as by initiating parenchymal ablation and the creation of a trough within the tissue. The tissue can be resected with a low power energy source such as a lower pressure water jet to selectively resect tissue and low for revealing and visualization of minor vessels 643. For example, glandular tissue can be selectively resected while vascular tissue remains intact. Examples of selective tissue removal and water jet flow rates to leave vascular tissue substantially intact are described in U.S. Pat. No. 10,251,665, filed on Nov. 25, 2015, granted Apr. 4, 2019, entitled "Multifluid tissue resection methods and devices", the entire disclosure of which is incorporated herein by reference. The selectively exposed blood vessels can be one or more of stapled, clipped or cauterized.

Figure 11:
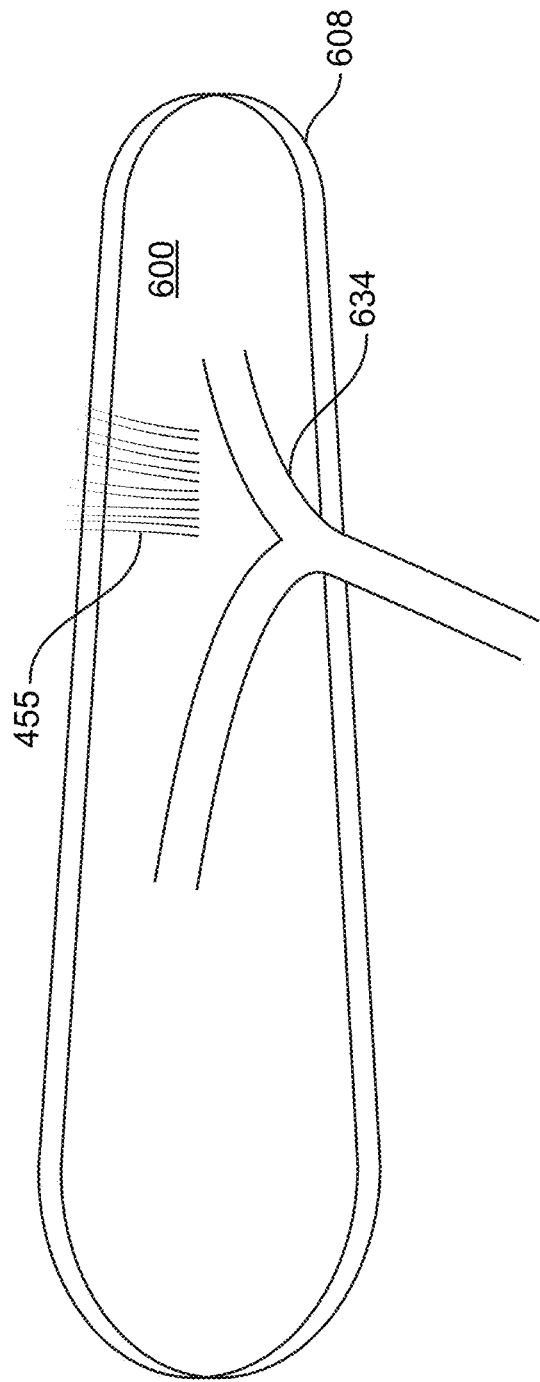
Figure 12:
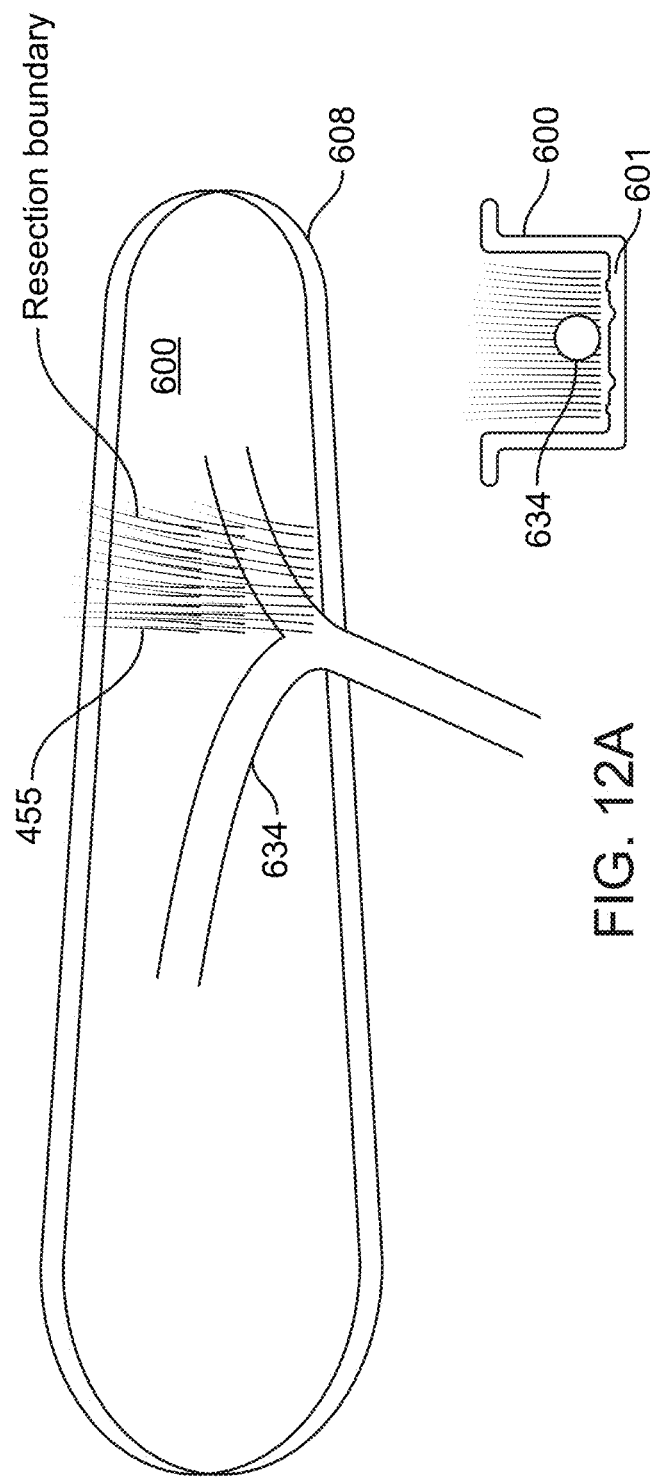

At a step shown in FIG. 11, selective tissue resection using, for example, jet ablation, with energy from an energy source 455, such as the water jet, continues to expose larger blood vessels 634 within the parenchymal tissue.

At a step shown in FIG. 12A, non-vascular tissue, such as parenchyma tissue is selectively resected to expose a blood vessel 634 with a supporting bed 601 of non-resected tissue as shown in FIG. 12B. These larger blood vessels 634 can be one or more of stapled, cut or cauterized. The tissue resection can continue through the remainder of the organ and a portion of the organ removed. The portion of the organ may comprise a lobe of the organ. The removed portion of the organ may comprise undesirable tissue or tissue suitable for tissue harvesting, e.g. organ donation, for example. In some embodiments, energy provided by the energy source and the energy source position may be controlled to allow parenchyma surrounding the blood vessels to eb ablated, revealing major vessels for dissection of the neuro vascular bundle and resultant staple closure of the remaining lobe. The harvested or transplant lobe may be discarded and/or anastomosis preparation may be performed.

Although FIGS. 9 to 12B illustrate a method of tissue resection and removal, donor tissue can be implanted with similar steps to prepare an organ to receive tissue.

Figure 13:
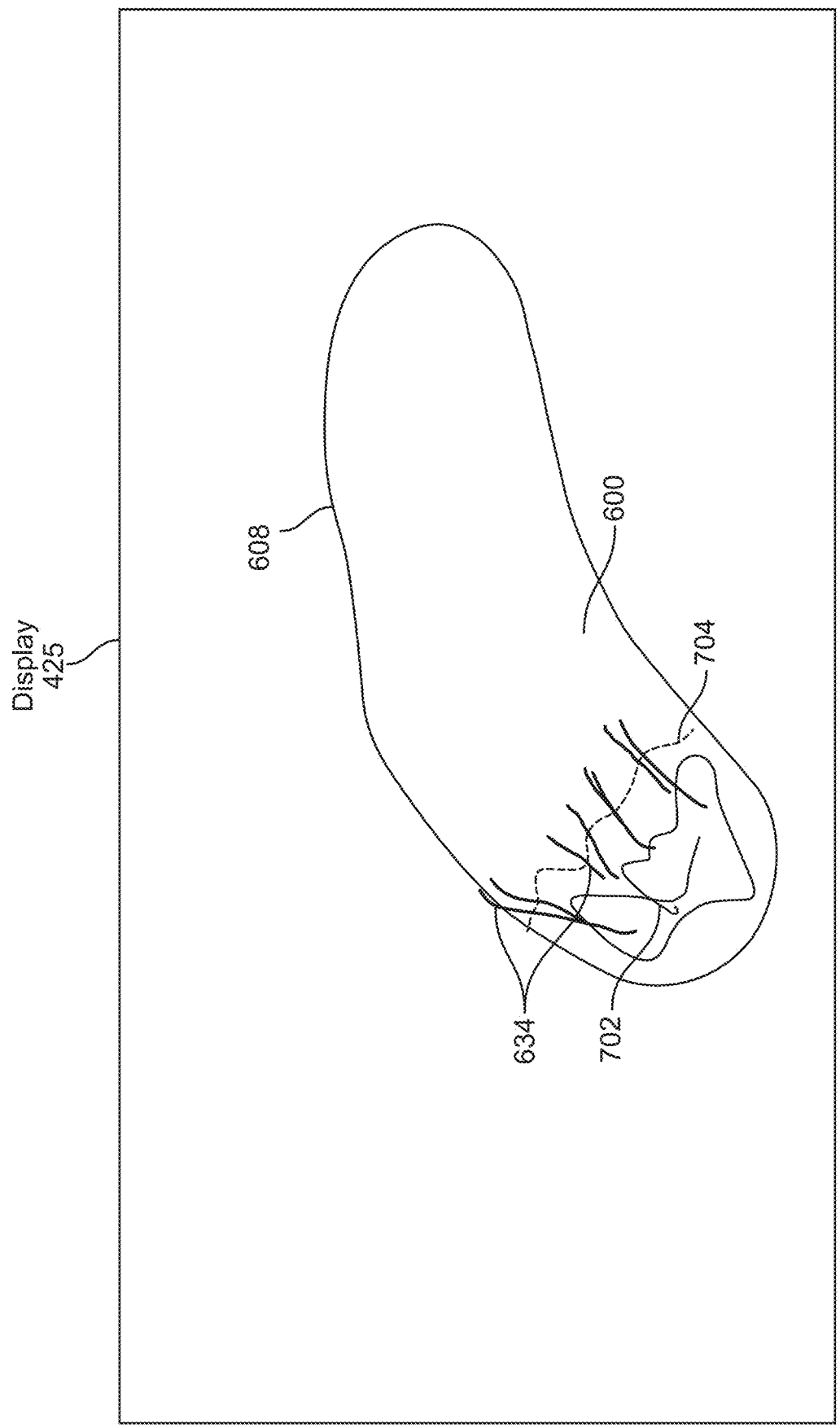
FIG. 13 shows selective tissue resection of and removal of undesirable tissue from an organ for 3D tissue removal with 3D volumetric imaging, in accordance with some embodiments.

FIG. 13 shows selective tissue resection and removal of undesirable tissue from an organ for 3D tissue removal with 3D volumetric imaging. The tissue of the organ can be imaged with volumetric imaging such as 3D tomography, for example ultrasound, CT scan, or MRI imaging. The image of the tissue to be resected can be shown on display 425 to a user. The user can select and identify the tissue 600 to be resected, the resection boundary 704 profile and blood vessels 634. For example, the user can use a touch screen display to input the tissue resection boundary. By providing a plurality of screens, the user can identify these structures on each of the plurality of screens so as to define a 3D tissue resection boundary, a 3D treatment profile, and a 3D shape profile of tissue not to be resected, such as a blood vessel, and a scan pattern 702 for tissue resection.

Figure 14:
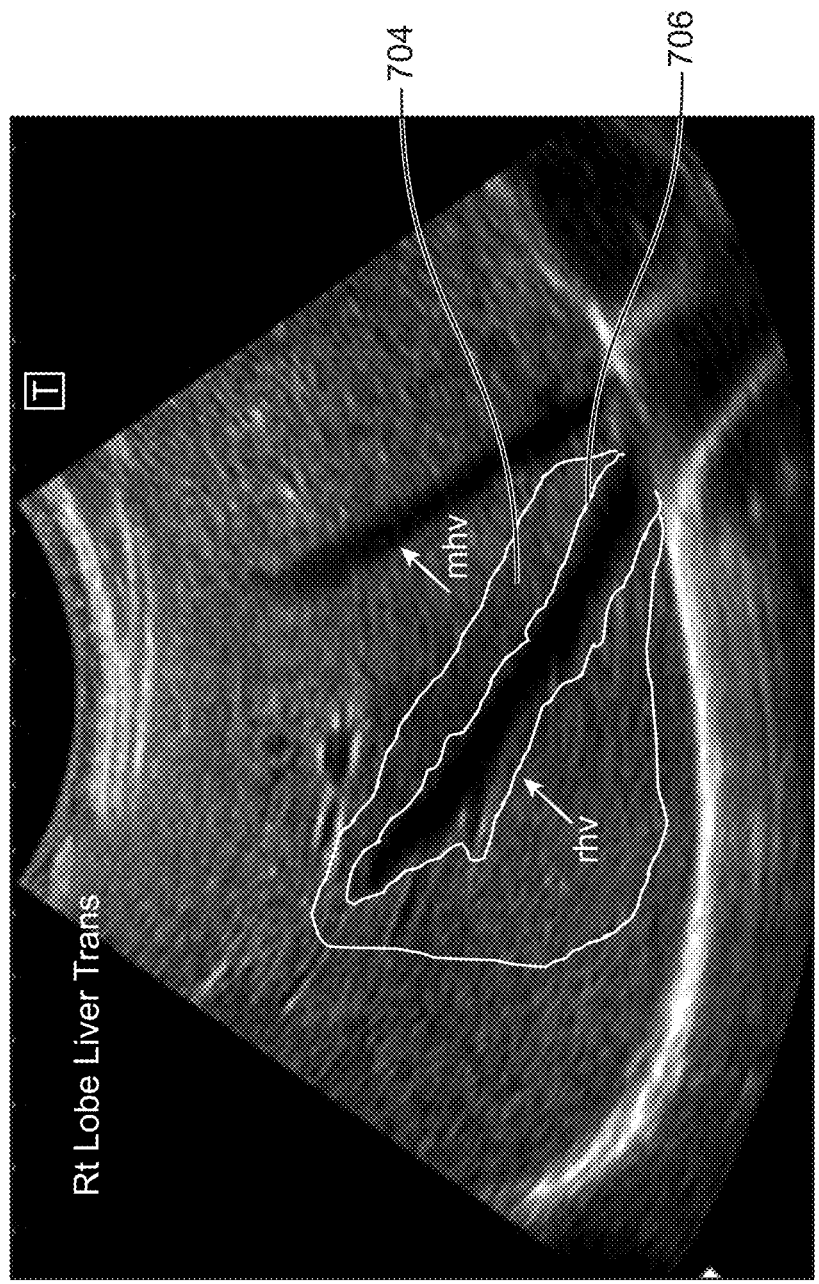
FIG. 14 shows an image of right and middle hepatic veins of a liver shown on a display for 3D tissue removal with 3D volumetric imaging, in accordance with some embodiments.

FIG. 14 shows an ultrasound image of a right hepatic vein (rhv) and middle hepatic vein (mhv) of a liver shown on a display for 3D tissue removal with 3D volumetric imaging. The image can be shown on a display, and the user can input the tissue resection boundary 704 around tissue not to be resected with the water source such as a blood vessel, along with the region 706 of tissue to be resected. In some embodiments, the tissue resection region extends around the boundary of the tissue not to be resected.

Figure 15:
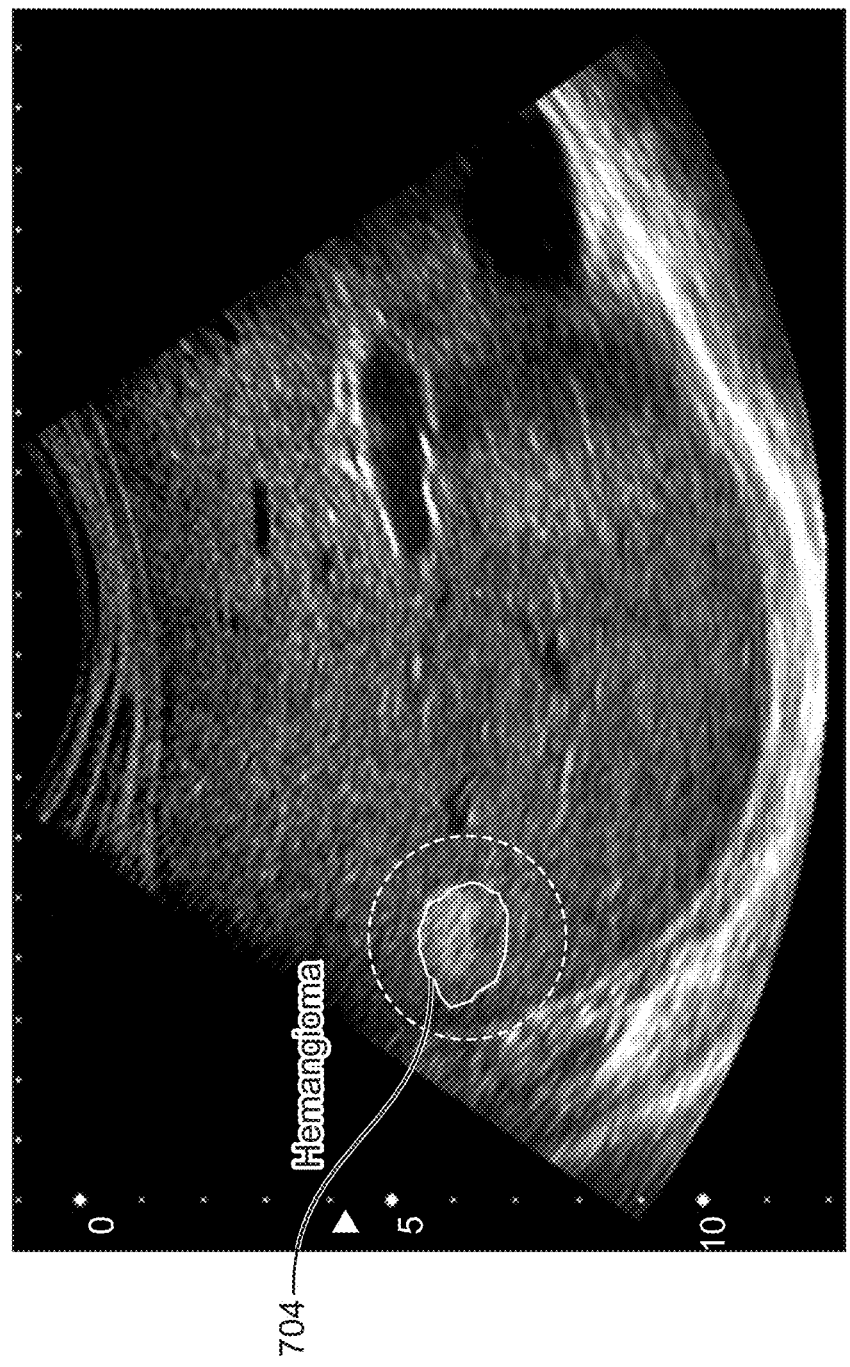
FIG. 15 shows an image of a hemangioma of a liver shown on a display for 3D tissue removal with 3D volumetric imaging, in accordance with some embodiments.

FIG. 15 shows an ultrasound image of a hemangioma of a liver shown on a display for 3D tissue removal with 3D volumetric imaging. The image can be shown on a display and the user can input the tissue resection boundary 704.

Figure 16:
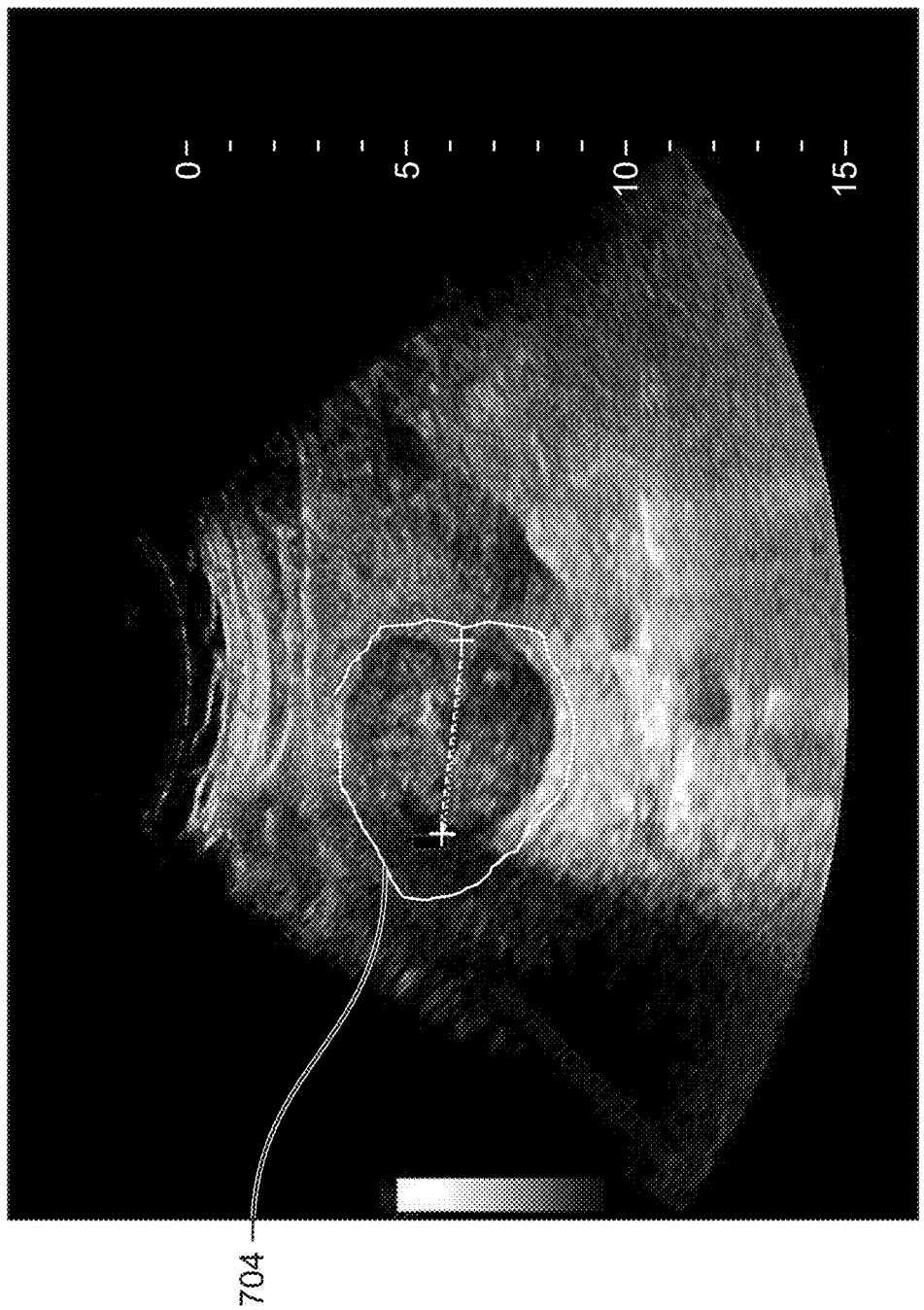
FIG. 16 shows an image of a liver cancer tumor shown on a display for 3D tissue removal away from the tumor with 3D volumetric imaging, in accordance with some embodiments.

FIG. 16 shows an ultrasound image of a liver cancer tumor shown on a display for 3D tissue removal with 3D volumetric imaging. The image can be shown on a display and the user can input the tissue resection boundary 704.

Figure 17:
FIG. 17 shows cirrhotic liver tissue for removal shown on a display for 3D tissue removal with 3D volumetric imaging, in accordance with some embodiments.

FIG. 17 shows cirrhotic liver tissue for removal shown on a display for 3D tissue removal with 3D volumetric imaging. The tissue removal boundary 704 and tissue removal region 706 are identified by the user on the display. The tissue can be resected along the tissue resection boundary and the cirrhotic tissue removed, for example with ablation by a water jet, or by removal of an intact portion of the cirrhotic liver which has been separated from the non-cirrhotic liver with the energy source.

Figure 18:
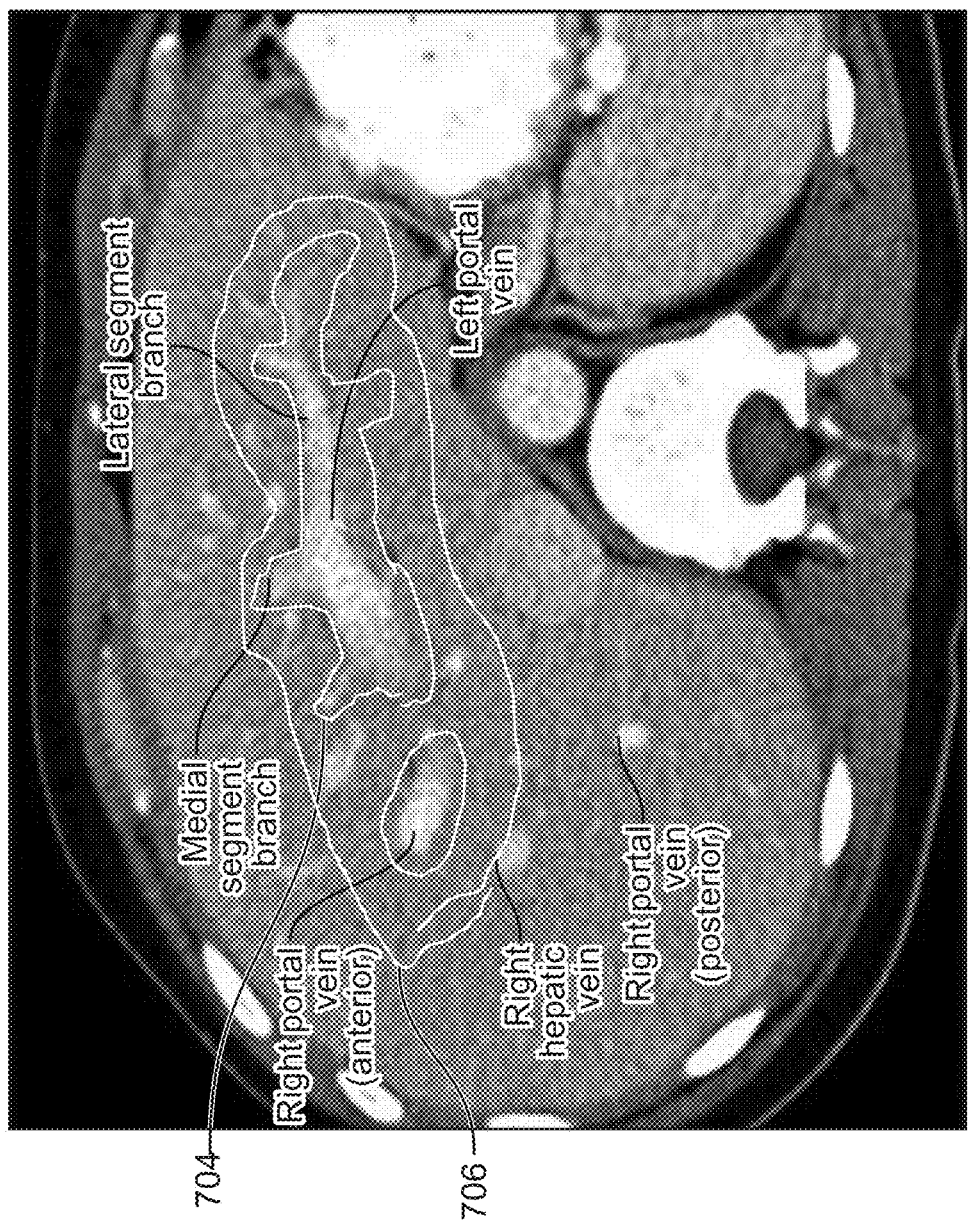
FIG. 18 shows a CT scan of liver tissue shown on a display for 3D tissue removal with 3D volumetric imaging, in accordance with some embodiments.
Figure 19A:
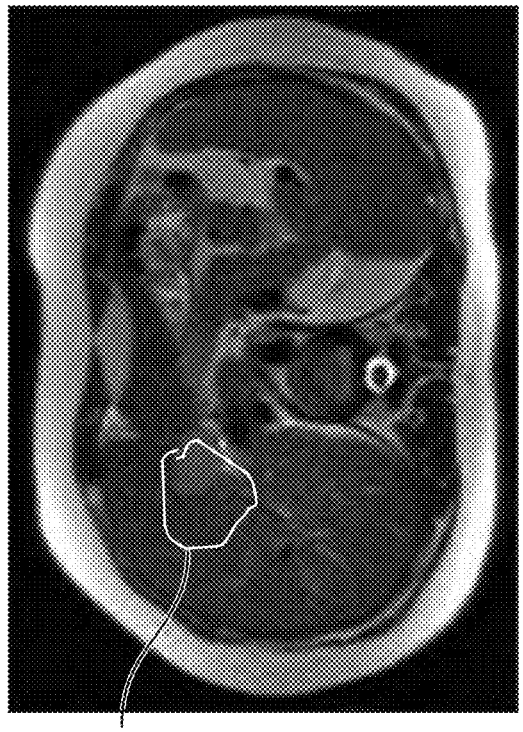
FIGS. 19A, 19B, 19C, and 19D show an MRI of a liver shown on a display for 3D tissue removal with 3D volumetric imaging, in accordance with some embodiments.
Figure 19B:
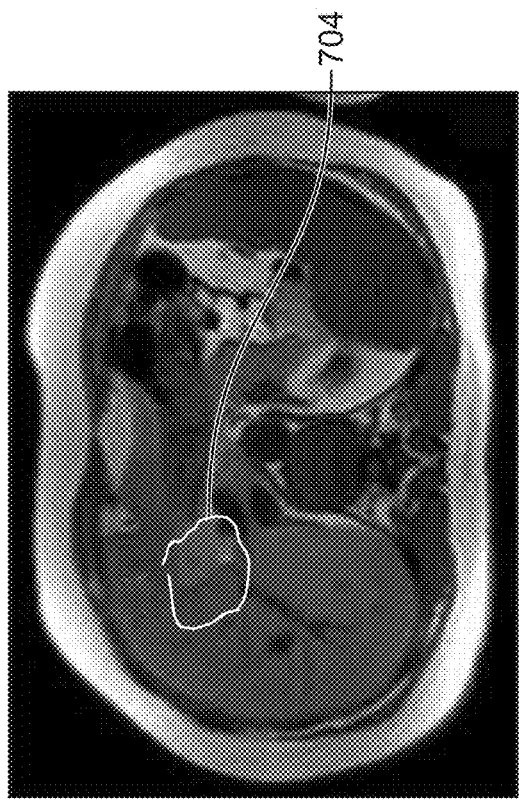
Figure 19C:
Figure 19D:

FIG. 18 shows a CT scan of liver tissue shown on a display for 3D tissue removal with 3D volumetric imaging. The user can input the tissue resection boundaries 704 around tissue not to be resected and the tissue resection regions 706.

FIGS. 19A-D show an MRI of a liver shown on a display for 3D tissue removal with 3D volumetric imaging and the resection boundaries 704 of tissue resection regions.

FIGS. 15 to 19 show images shown on a display to generate tissue resection profiles and boundaries. A processor can be configured with instructions to perform volumetric resection in many ways. For example, the images may comprise tomographic images, in which the user views a plurality of image slices and identifies one or more of the tissue resection profile 700, the tissue resection region 706, or the tissue resection boundary 704 of the tissue not to be resected. The boundary of the tissue not to be resected can be located within a boundary of a tissue resection region. For each of the plurality of slices, the user can identify each of the one or more regions. In some embodiments, an artificial intelligence algorithm such as a convolutional neural network can be trained and used to identify one or more of the boundaries, e.g. a boundary of a blood vessel, from each of the plurality of images. From identified regions of each of the plurality of slices, the process can generate 3D one or more of a 3D tissue resection profile, a 3D tissue resection region, or a 3D tissue resection boundary of the tissue not to be resected within a boundary of a tissue resection region. Once the 3D volumetric resection regions, tissue resection boundaries and tissue sparing regions have been identified, the processor can be configured with instructions to move the robotic arm to a plurality of locations to remove tissue as described herein.

While the tissue can be imaged in many ways, in some embodiments, the tissue is imaged with ultrasound to identify cancerous tissue, such as ultrasound shear wave elastography. The tissue can be imaged with Doppler ultrasound or 3D doppler ultrasound to identify blood vessels. The ultrasound transducers can be located near a tip of the treatment probe 450, for example. Alternatively or in combination, the ultrasound transducers can be coupled to the patient with another ultrasound probe or an external ultrasound transducer.

In some embodiments, the fluid released into the organ or fluid filled enclosure comprises a chemotherapeutic agent. For example, the fluid released with the water jet comprises a chemotherapeutic agent.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of" Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. An apparatus for tissue resection comprising: a robotic arm; a treatment probe comprising an energy source coupled to the robotic arm; and a processor coupled to the robotic arm to position the probe.

Clause 2. The apparatus of clause 1, wherein the robotic arm is configured to move a proximal end of the probe with 3 or more degrees of freedom to position the energy source with a position and orientation to resect tissue and optionally wherein the energy source comprises a water jet.

Clause 3. The apparatus of clause 1, wherein the robotic arm is configured to move a proximal end of the probe to position the energy source.

Clause 4. The apparatus of clause 3, wherein the treatment probe comprises a stiff treatment probe.

Clause 5. The apparatus of clause 1, wherein the robotic arm is configured to rotate the probe about an elongate axis extending along the probe.

Clause 6. The apparatus of clause 1, wherein the treatment probe is configured to rotate about an elongate axis of the probe while a pose of the robotic arm remains fixed.

Clause 7. The apparatus of clause 1, wherein the energy source comprises a water jet orientated transverse to an elongate axis of the probe to release the water jet to a side of the probe.

Clause 8. The apparatus of clause 1, wherein the energy source comprises a water jet orientated along an elongate axis of the probe to release the water jet to toward the tissue in a direction along the elongate axis.

Clause 9. The apparatus of clause 1, wherein the treatment probe comprises an irrigation lumen, an endoscope, a high-pressure lumen coupled to a water jet and an aspiration lumen to remove resected tissue.

Clause 10. The apparatus of clause 1, wherein the treatment probe comprises an irrigation lumen, an endoscope, a high-pressure lumen coupled to a nozzle to release a water jet, an ultrasound transducer and an aspiration lumen to remove resected tissue.

Clause 11. The apparatus of clause 1, wherein the energy source comprises a water jet to release the water jet from an orifice at a flow rate to remove glandular tissue faster than collagenous tissue and optionally wherein the collagenous tissue comprises vascular tissue.

Clause 12. The apparatus of clause 11, wherein the processor comprises instructions to remove the tissue with a plurality of successive layers, wherein each of the plurality of successive layers is removed with a scan pattern of the water jet.

Clause 13. The apparatus of clause 12, wherein the processor is configured with instructions to move a distal end of the arm with a movement corresponding to the scan pattern for each of the plurality of layers.

Clause 14. The apparatus of clause 13, wherein the processor is configured with instructions to move the distal end of the arm to advance the probe for resection of a subsequent layer.

Clause 15. The apparatus of clause 13, wherein the processor is configured with instructions to increase a flow rate of water jet for resection of a subsequent layer.

Clause 16. The apparatus of clause 1, wherein the processor is configured with instructions to move the distal end of the arm to advance the probe along a tissue resection boundary and wherein the processor is configured to orient the distal end of the arm to orient the probe to extend along the tissue resection boundary.

Clause 17. The apparatus of clause 1, further comprising an enclosure comprising a barrier material to provide a fluid filled environment on a surface of the tissue.

Clause 18. The apparatus of clause 17, wherein the enclosure comprises an aperture to receive the treatment probe.

Clause 19. The apparatus of clause 17, wherein the processor comprises instructions to pivot the treatment probe near an aperture of the enclosure sized to receive the treatment probe.

Clause 20. The aperture of clause 17, wherein the treatment probe comprises a lumen sized to extend through an aperture into the enclosure to provide fluid within the enclosure and wherein the treatment probe comprises an aspiration lumen sized to extend into the enclosure and remove tissue resection products.

Clause 21. The apparatus of clause 1, wherein the treatment probe comprises an elongate probe sized to extend from an incision in a skin of a patient to an organ.

Clause 22. The apparatus of clause 1, wherein the treatment probe comprises an elongate probe sized to extend from an external orifice to an organ.

Clause 23. The apparatus of clause 1, wherein the processor is configured with instructions to move and orient the distal end of the arm to pivot the probe between a proximal end of the probe and a distal end of the probe to decrease probe movement at the pivot.

Clause 24. The apparatus of clause 23, wherein the processor is configured with instructions to receive an input corresponding to a location of a blood vessel and wherein the processor is configured with instructions to pivot the probe at a location away from the blood vessel.

Clause 25. The apparatus of clause 23, wherein the processor is configured with instructions to receive an input corresponding to a location near a pubic bone and wherein the processor is configured with instructions to pivot the probe at the location to decrease movement of the probe near the pubic bone.

Clause 26. The apparatus of clause 1, wherein the treatment probe comprises an elongate probe sized to extend from an opening of a urethra to a prostate and wherein the processor is configured with instructions to pivot the probe at a location near one or more of a verumontanum of the prostate, an external sphincter of the urethra or a location between the verumontanum or the external sphincter.

Clause 27. The apparatus of clause 1, wherein a portion of the probe proximal to the pivot location is configured to move in a direction opposite of a distal end of the probe, and optionally wherein an external opening to the urethra moves in the direction opposite the distal end of the probe.

Clause 28. The apparatus of clause 1, wherein the probe comprises a deflectable tip portion.

Clause 29. The apparatus of clause 28, wherein the deflectable tip portion comprises a flexible tip portion.

Clause 30. The apparatus of clause 28, wherein deflectable tip is configured to separate glandular tissue from capsular tissue along a tissue interface.

Clause 31. The apparatus of clause 28, wherein deflectable tip is configured to deflect in response to a user input to the processor and optionally wherein the deflectable tip comprises a plurality of elongate elements to deflect the tip in response to the user input.

Clause 32. The apparatus of clause 28, wherein deflectable tip comprises a lumen and a nozzle to release a fluid stream and optionally wherein the lumen comprises a high pressure lumen and the fluid stream comprises a water jet released from the nozzle.

Clause 33. The apparatus of clause 1, wherein the probe is configured for insertion of one or more of brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat.

Clause 34. The apparatus of clause 1, wherein the processor comprises to present an image of an organ to a user on a display and to receive input from the user to identify one or more of a tissue resection boundary, a region of tissue to be resected or a region of tissue not to be resected and optionally wherein the region of tissue not to be resected is within a boundary of the tissue to be resected.

Clause 35. The apparatus of clause 1, wherein the processor comprises instructions to provide a plurality of images to a user, the plurality of images comprising a plurality of tomographic image slices, and wherein the processor is configured to receive input from the user for the plurality of images and to generate one or more of a 3D tissue resection boundary, a 3D region of tissue to be resected or a 3D region of tissue not to be resected and optionally wherein the 3D region of tissue not to be resected is within a 3D boundary of the tissue to be resected.

Clause 36. The apparatus of clause 1, wherein the processor comprises instructions to receive a plurality of images of a patient, the plurality of images comprising a plurality of tomographic image slices, and wherein the processor is configured to identify one or more of a tissue resection boundary, a region of tissue to be resected or a region of tissue not to be resected and optionally wherein the region of tissue not to be resected is within a boundary of the tissue to be resected the plurality of images.

Clause 37. The apparatus of clause 36, wherein the processor is configured with instructions to generate one or more of a 3D tissue resection boundary, a 3D region of tissue to be resected or a 3D region of tissue not to be resected and optionally wherein the 3D region of tissue not to be resected is within a 3D boundary of the tissue to be resected.

Clause 38. A method, the method comprising providing or using the apparatus of any one of the preceding clauses.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. An apparatus for tissue removal comprising:
    a robotic arm comprising a distal end and a plurality of articulating joints, where the plurality of articulating joints provide for movement of the distal end of the robotic arm in a plurality of degrees of freedom;
    a treatment probe comprising an energy source, the treatment probe being coupled to the distal end of the robotic arm; and
    a processor coupled to the robotic arm to position the treatment probe, the processor configured cause a proximal end of the treatment probe to move along a path and to move a distal end of the treatment probe along a corresponding path about a pivot located therebetween and wherein the processor is configured to advance the treatment probe along a tissue removal boundary and wherein the processor is configured to orient the treatment probe to extend along the tissue removal boundary.

2. The apparatus of claim 1, wherein the robotic arm is configured to move a proximal end of the treatment probe to position the energy source with a position and orientation to remove tissue.

3. The apparatus of claim 1, wherein the robotic arm is configured to move a proximal end of the treatment probe to position the energy source.

4. The apparatus of claim 3, wherein the treatment probe comprises a stiff treatment probe.

5. The apparatus of claim 1, wherein the robotic arm is configured to rotate the treatment probe about an elongate axis extending along the treatment probe.

6. The apparatus of claim 1, wherein the treatment probe is configured to rotate about an elongate axis of the treatment probe while a pose of the robotic arm remains fixed.

7. The apparatus of claim 1, wherein the energy source comprises a water jet orientated transverse to an elongate axis of the treatment probe to release the water jet to a side of the treatment probe.

8. The apparatus of claim 1, wherein the energy source comprises a water jet orientated along an elongate axis of the treatment probe to release the water jet toward tissue in a direction along the elongate axis.

9. The apparatus of claim 1, wherein the treatment probe comprises an irrigation lumen, an endoscope, a high-pressure lumen coupled to a water jet and an aspiration lumen to remove treated tissue.

10. The apparatus of claim 1, wherein the treatment probe comprises an irrigation lumen, an endoscope, a high-pressure lumen coupled to a nozzle to release a water jet, an ultrasound transducer and an aspiration lumen to remove treated tissue.

11. The apparatus of claim 1, wherein the energy source comprises an orifice to release a water jet from an orifice at a flow rate to remove glandular tissue faster than collagenous tissue.

12. The apparatus of claim 11, wherein the processor is configured to remove tissue in a plurality of successive layers, wherein each of the plurality of successive layers is removed with a scan pattern of the water jet.

13. The apparatus of claim 12, wherein the processor is configured to move the distal end of the robotic arm with a movement corresponding to the scan pattern.

14. The apparatus of claim 13, wherein the processor is configured to move the distal end of the robotic arm to advance the treatment probe for removal of a subsequent layer.

15. The apparatus of claim 13, wherein the processor is configured to increase a flow rate of the water jet for removal of a subsequent layer.

16. The apparatus of claim 1, further comprising an enclosure comprising a barrier material to provide a fluid filled environment on a surface of tissue.

17. The apparatus of claim 16, wherein the enclosure comprises an aperture to receive the treatment probe.

18. The apparatus of claim 16, wherein the processor is configured to pivot the treatment probe near an aperture of the enclosure sized to receive the treatment probe.

19. The apparatus of claim 16, wherein the treatment probe comprises a lumen sized to extend through an aperture into the enclosure to provide fluid within the enclosure and wherein the treatment probe comprises an aspiration lumen sized to extend into the enclosure and remove treated tissue products.

20. The apparatus of claim 1, wherein the processor is configured to receive an input corresponding to a location near a pubic bone and wherein the processor is configured to pivot the treatment probe at the location to decrease movement of the treatment probe near the pubic bone.

21. The apparatus of claim 1, wherein a portion of the treatment probe proximal to the pivot location is configured to move in a direction opposite of a distal end of the treatment probe and configured to move an external opening to a urethra in the direction opposite the distal end of the treatment probe.

* * * * *